United States Patent
Ueda

(10) Patent No.: US 10,881,848 B2
(45) Date of Patent: Jan. 5, 2021

(54) CONNECTOR, INFUSION SET, AND MEDICAL DEVICE CONNECTABLE TO CONNECTOR

(71) Applicant: TERUMO KABUSHIKI KAISHA, Tokyo (JP)

(72) Inventor: Yasuhiro Ueda, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 77 days.

(21) Appl. No.: 15/938,781

(22) Filed: Mar. 28, 2018

(65) Prior Publication Data
US 2018/0214683 A1    Aug. 2, 2018

Related U.S. Application Data

(63) Continuation of application No. PCT/JP2016/004343, filed on Sep. 26, 2016.

(30) Foreign Application Priority Data

Sep. 29, 2015 (JP) ................................. 2015-191375

(51) Int. Cl.
*A61M 39/10* (2006.01)
*A61M 39/20* (2006.01)
(Continued)

(52) U.S. Cl.
CPC ........ *A61M 39/1011* (2013.01); *A61M 39/10* (2013.01); *A61M 39/20* (2013.01);
(Continued)

(58) Field of Classification Search
CPC .. A61M 39/10; A61M 39/1011; A61M 39/20; A61M 39/26; A61M 39/165;
(Continued)

(56) References Cited

U.S. PATENT DOCUMENTS 4,123,091 A * 10/1978 Cosentino ........... F16L 37/0847
285/39
4,557,508 A * 12/1985 Walker .................. E21B 33/038
285/84
(Continued)

FOREIGN PATENT DOCUMENTS

| JP | H03-94770 A | 4/1991 |
| JP | 2004-000483 A | 1/2004 |
| WO | WO-2012/128321 A1 | 9/2012 |

OTHER PUBLICATIONS

International Search Report with English translation and Written Opinion issued in International Application No. PCT/JP2016/004343 dated Dec. 13, 2016.

*Primary Examiner* — Kami A Bosworth
*Assistant Examiner* — Antarius S Daniel
(74) *Attorney, Agent, or Firm* — Foley & Lardner LLP

(57) ABSTRACT

A connector is connectable to a medical device that includes a female connector portion. The connector includes: a main body member including: a cylinder portion that is insertable into the female connector portion, and a lock portion configured to, upon insertion of the cylinder portion into the female connector portion, pass over part of the medical device and then move in a predetermined locking direction to lock the medical device; and a lock member that is movable with respect to the main body member. When the main body member is in a state in which the lock portion locks the medical device, the lock member is moveable to a lock position at which the lock member limits movement of the lock portion in a predetermined unlocking direction.

6 Claims, 12 Drawing Sheets

(51) Int. Cl.
  *A61M 5/158* (2006.01)
  *A61M 5/162* (2006.01)
  *A61M 39/24* (2006.01)
  *A61M 39/22* (2006.01)

(52) U.S. Cl.
  CPC ............ *A61M 5/158* (2013.01); *A61M 5/162* (2013.01); *A61M 39/24* (2013.01); *A61M 2039/229* (2013.01); *A61M 2039/2426* (2013.01); *A61M 2207/00* (2013.01)

(58) Field of Classification Search
  CPC .. A61M 2039/1027; A61M 2039/1066; A61M 2039/2426; A61M 2039/2433; F16L 37/00; F16L 39/08; F16L 39/084
  See application file for complete search history.

(56) References Cited

U.S. PATENT DOCUMENTS

| | | |
|---|---|---|
| 4,895,570 A | 1/1990 | Larkin |
| 5,437,650 A | 8/1995 | Larkin et al. |
| 2014/0088432 A1* | 3/2014 | Ryan ................ A61B 10/0283 600/471 |

* cited by examiner

CONNECTOR, INFUSION SET, AND MEDICAL DEVICE CONNECTABLE TO CONNECTOR

CROSS-REFERENCE TO RELATED APPLICATIONS

The present application is a bypass continuation of PCT Appl. No. PCT/JP2016/004343, filed on Sep. 26, 2016, which claims priority to Japanese Appl. No. 2015-191375, filed on Sep. 29, 2015. The contents of these applications are hereby incorporated by reference in their entireties.

BACKGROUND

The present disclosure relates to a connector, an infusion set, and a medical device connectable to the connector.

To provide an infusion such as a nutritional supplement or a medical fluid to a patient, there is the need to form a path for conveying the infusion (infusion line). The infusion line is generally formed by connecting infusion tubes and various medical devices. Conventionally, a connector is used to interconnect these different members. The connection of connectors is normally established by inserting the male connector portion of one connector into the female connector portion of the other connector. It is also known that the positions of the connectors are fixed with the male connector portion inserted into the female connector portion for the purpose of inhibiting the connected connectors from being unintentionally separated from each other.

JP 2004-000483 A and WO 2012/128321 A1 disclose the use of a plurality of claws as lock portions to fix the positions of the connected connectors. According to these publications, when the male connector portion of one connector is inserted into the female connector portion of the other connector, the claws of the one connector elastically deform and pass over the step portions in the other connector and then restore the original shape to inhibit the one connector from coming off from the step portions in the other connector.

SUMMARY

The one connector described in JP 2004-000483 A is configured to lock the other connector only by the lock lever with the claws. Accordingly, it is necessary to increase the force of pressing the other connector by the lock lever to a degree that the unintended separation of the connectors can be inhibited. Therefore, at connection and disconnection of the connectors, it is necessary to exert relatively large force for operating the lock lever against the pressing force of the lock lever.

In this regard, the one connector described in WO 2012/128321 A1 includes, separately from the engagement member with the plurality of claws, a lock member covering the circumference of the engagement member to inhibit the other connector from being unintentionally released. Therefore, the pressing force of the engagement member for locking the other connector can be made relatively small.

In the connectors described in WO 2012/128321 A1, however, at connection of the connectors, the lock member is likely to move from the engagement member. Accordingly, the plurality of claws of the engagement member in the one connector may move to the position limiting the elastic deformation of the claws in the radial outward direction before or while the claws pass over the step portions in the other connector. In such a case, when the claws pass over the step portions, the pressing force of the claws on the step portions becomes large so that the claws and the step portions are likely to be shaved off. This may cause performance degradation due to repeated use.

One object of certain embodiments described herein is to provide a connector that can be easily connected to a medical device and inhibit performance degradation due to repeated use, an infusion set, and a medical device connectable to the connector.

According to one embodiment, a connector is connectable to a medical device with a female connector portion. The connector includes: a main body member having a cylinder portion that is insertable into the female connector portion of the medical device and a lock portion that, at the insertion of the cylinder portion into the female connector portion, passes over part of the medical device and then moves in a predetermined locking direction to lock the medical device; and a lock member that is movable with respect to the main body member and is movable in the state where the lock portion locks the medical device to a lock position in which to limit the movement of the lock portion locking the medical device in a predetermined unlocking direction different from the predetermined locking direction. The main body member includes a movement inhibition portion that inhibits the movement of the lock member to the lock position while the lock portion passes over the part of the medical device.

In one aspect, an insertion direction of the cylinder portion into the female connector portion is codirectional with a movement direction of the lock member to the lock position. At the insertion of the cylinder portion into the female connector portion, the movement inhibition portion is opposed to an abutment portion of the lock member in the insertion direction while the lock portion passes over the part of the medical device. When abutting with the abutment portion, the movement inhibition portion serves as an abutment wall that inhibits the movement of the lock member to the lock position. In one aspect, when the lock portion passes over the part of the medical device and moves in the predetermined locking direction, the abutment wall is not opposed to the abutment portion of the lock member in the insertion direction and permits the movement of the lock member to the lock position.

In one aspect, the lock portion is positioned outside the cylinder portion in the radial direction of the cylinder portion and the predetermined locking direction is inward in the radial direction.

In one aspect, the main body member includes a deformation portion that extends in the insertion direction at a position outside the cylinder portion in the radial direction and is elastically deformable in the radial direction, and an engagement member that is fixed in position with respect to the cylinder portion. In one aspect, the lock member is positioned outside the engagement member in the radial direction, the lock portion is a lock claw that protrudes inward from the deformation portion in the radial direction, and the abutment wall is formed on an outer wall of the deformation portion in the radial direction.

In one aspect, the lock member includes a reception portion that can receive at least part of the deformation portion elastically deformed in the radial direction, and the abutment portion is provided in the reception portion.

In another embodiment, an infusion set includes the connector.

In another embodiment, a medical device includes the female connector portion to which the connector is connectable. The female connector portion is at least partly formed by a cap that defines an insertion opening into which the cylinder portion is inserted and a holder that defines a flow path communicating with the insertion opening and supports the cap. The cap includes a first slide portion that the lock portion slides on and passes over at the insertion of the cylinder portion into the insertion opening. The cap or the holder includes a second slide portion that the lock portion slides on and passes over when the lock portion moves in the predetermined unlocking direction after having passed over the first slide portion and moved in the predetermined locking direction.

In one aspect, the predetermined locking direction is inward in the radial direction of the cylinder portion, the predetermined unlocking direction is the outer radial direction of the cylinder portion, and the second slide portion is adjacent to the lock portion having passed over the first slide portion and moved in the inner direction in a circumferential direction of the cylinder portion.

In one aspect, the cap is formed from a material harder than the holder and the second slide portion is provided in the cap.

According to certain embodiments describe herein, it is possible to provide a connector that can be easily connected to a medical device and inhibit performance degradation due to repeated use, an infusion set, and a medical device connectable to the connector.

DETAILED DESCRIPTION

Figure 1A:
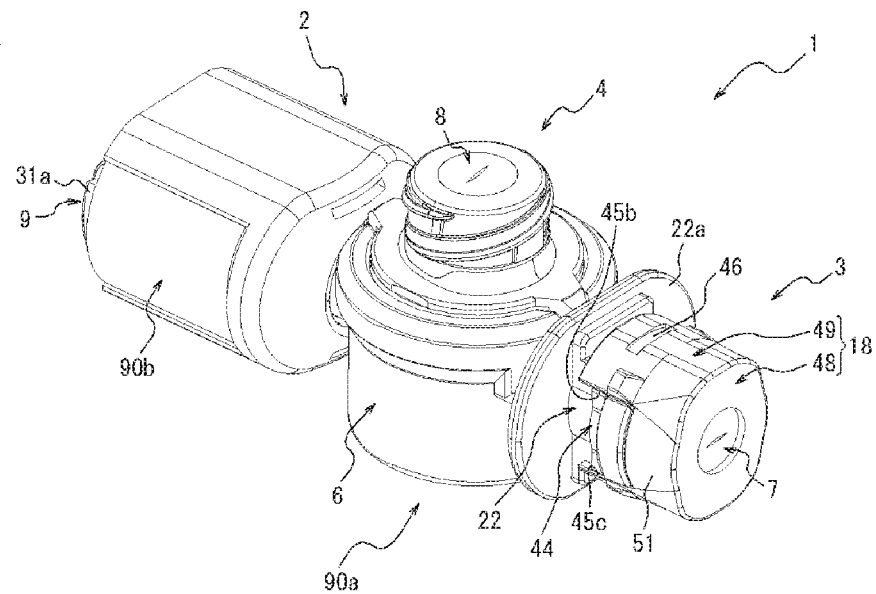
FIGS. 1A and 1B are perspective views of a connector according to an embodiment of the present invention.

Embodiments of a connector, an infusion set, and a medical device connectable to the connector according to the present invention will be described below with reference to FIGS. 1 to 13. The same members and components in the drawings are given the same reference signs.

Figure 1B:
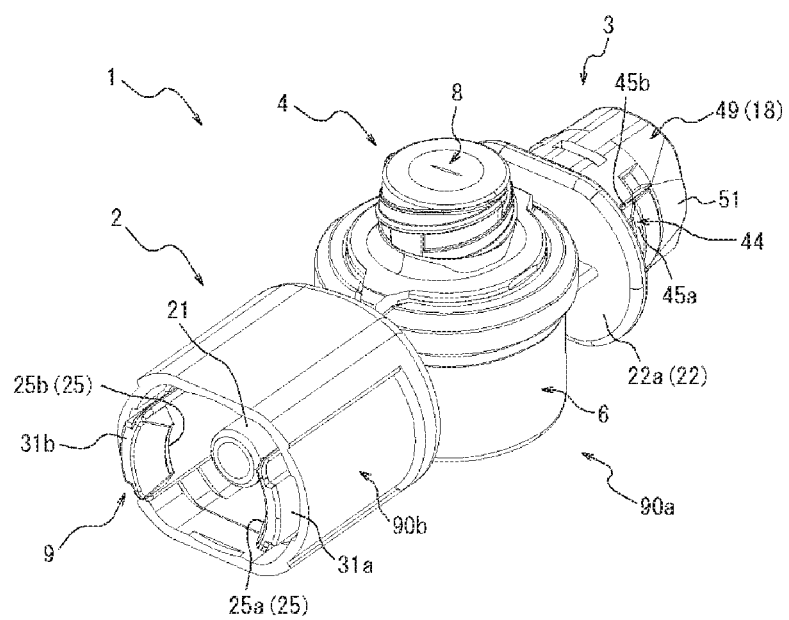

FIGS. 1A and 1B is a perspective view of a connector 1 as an embodiment of a connector according to the present invention, and FIGS. 1A and 1B illustrate the connector 1 seen from different viewpoints. As illustrated in FIG. 1, the connector 1 includes a male connector portion 2, a first female connector portion 3, and a second female connector portion 4. More specifically, the connector 1 of the embodiment includes the first female connector portion 3 as an upstream port portion, the male connector portion 2 as a downstream port portion, and the second female connector portion 4 as a coinfusion port portion.

Figure 2A:
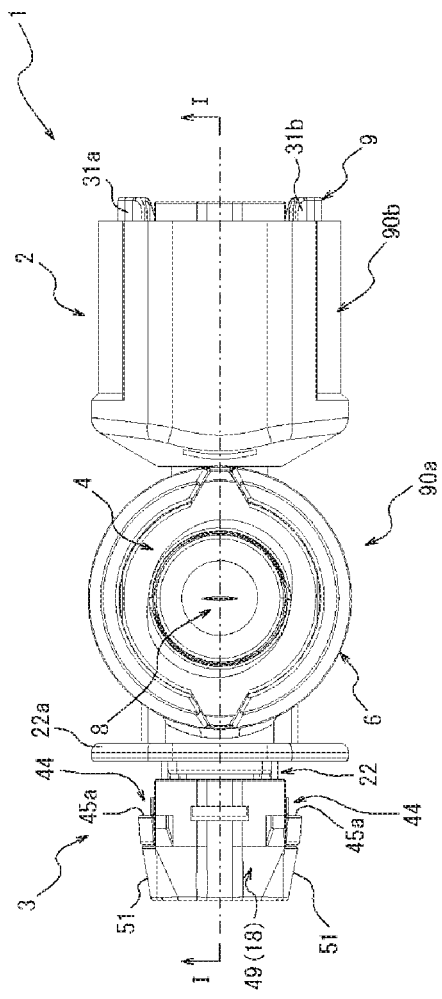
FIG. 2A is a view of the connector illustrated in FIGS. 1A and 1B seen from the top of a second female connector portion.
Figure 2B:
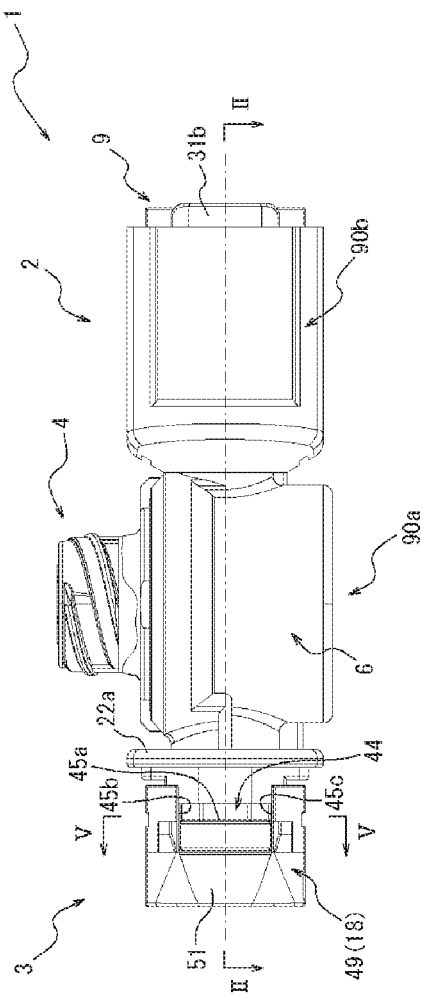
FIG. 2B is a view of the connector illustrated in FIGS. 1A and 1B seen from a side of the second female connector portion.
Figure 3:
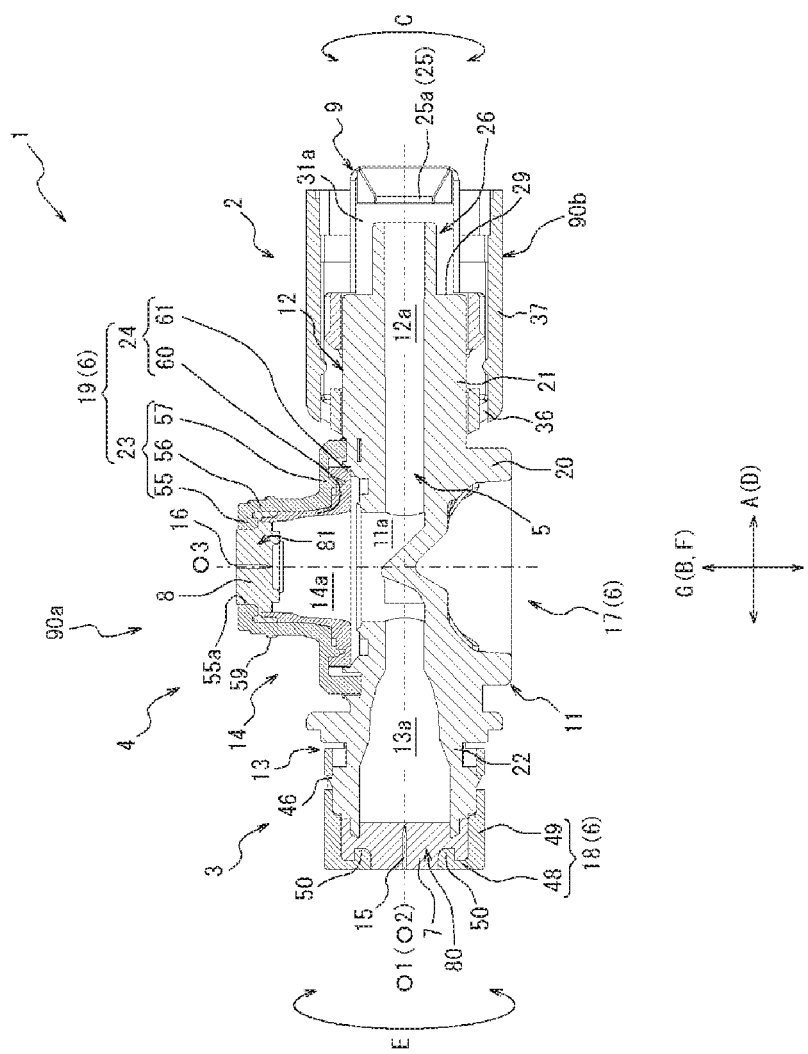
FIG. 3 is a cross-sectional view of FIG. 2A taken along line I-I.

FIG. 2A is a view of the connector 1 seen from the top of the second female connector portion 4, and FIG. 2B is a view of the connector 1 seen from a side of the second female connector portion 4. FIG. 3 is a cross-sectional view of FIG. 2A taken along line I-I, and FIG. 4 is a cross-sectional view of FIG. 2B taken along line II-II.

Figure 4:
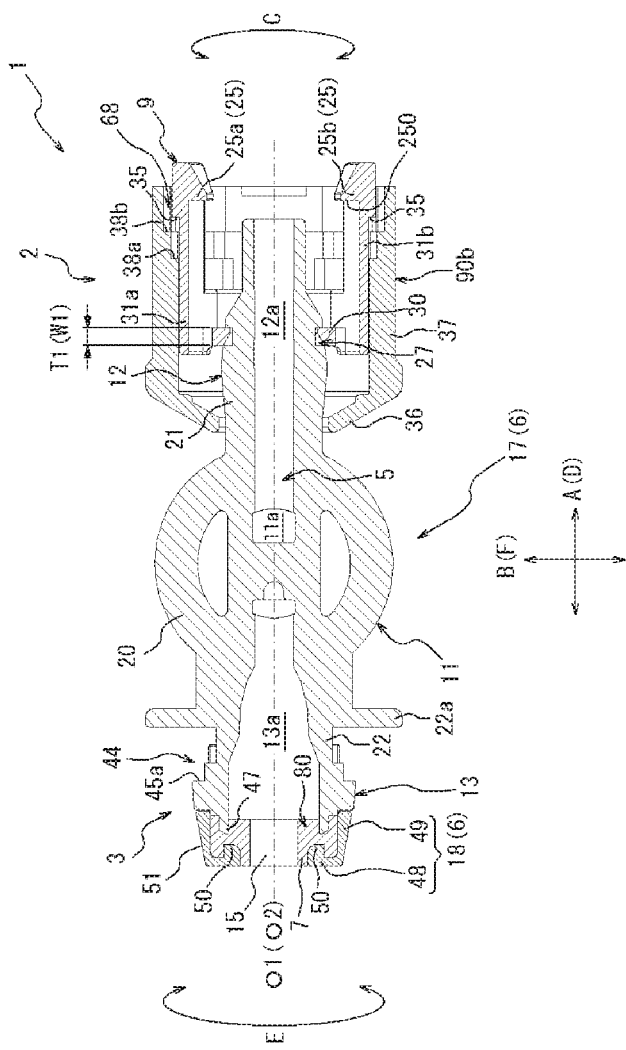
FIG. 4 is a cross-sectional view of FIG. 2B taken along line II-II.

As illustrated in FIGS. 1 to 4, the first female connector portion 3 and the second female connector portion 4 are different in shape. The male connector portion 2 is shaped to be connectable to a female connector portion in another medical device equal in shape to the first female connector portion 3, and is shaped not to be connectable to a female connector portion in another medical device equal in shape to the second female connector portion 4. Accordingly, to connect a plurality of connectors 1, for example, the male connector portion 2 of one connector 1 and the first female connector portion 3 of another connector 1 are connected together. The connection between the male connector portion 2 and a female connector portion 3' equal in shape to the first female connector portion 3 will be described later (see FIG. 10). As illustrated in FIGS. 3 and 4, the connector 1 defines a flow path 5 therein.

Herein, the "connectable shape" of the male connector portion to the female connector portion means the shape of the male connector portion that can be connected to the female connector portion in a liquid-tight manner such that an infusion such as a medical fluid does not leak at the portion of connection to the female connector portion. In addition, the "non-connectable shape" of the male connector portion to the female connector portion means the shape of the male connector portion that cannot be connected to the female connector portion in a liquid-tight manner such that an infusion does not leak at the portion of connection to the female connector portion.

Further, the "medical device" is not limited to medical connectors such as a connector equal in shape to the connector 1 and a connector different in shape from the connector 1 but includes a medical tube and a syringe having a female connector portion equal in shape to the first female connector portion 3 and a female connector portion equal in shape to the second female connector portion 4, for example.

As illustrated in FIGS. 1 to 4, in the connector 1 of the embodiment, the male connector portion 2 is provided at one end side of the connector 1, the first female connector portion 3 is provided at the other end side of the connector 1, and the second female connector portion 4 is provided at a position in the connector 1 different from the positions of the male connector portion 2 and the first female connector portion 3.

Specifically, as illustrated in FIGS. 3 and 4, in the embodiment, a central axis line O1 of a first cylinder portion 12 described later in the male connector portion 2 is almost equal to a central axis line O2 of an inner wall defining a first insertion opening 80 described later in the first female connector portion 3. In the embodiment, the central axis line of the male connector portion 2 is almost equal to the central axis line O1 of the first cylinder portion 12 in the male connector portion 2, and the central axis line of the first female connector portion 3 is almost equal to the central axis line O2 of the inner wall defining the first insertion opening 80. Accordingly, the central axis line of the male connector portion 2 and the central axis line of the first female connector portion 3 are also almost equal to each other.

As illustrated in FIG. 3, in the embodiment, a central axis line O3 of an inner wall defining a second insertion opening 81 described later in the second female connector portion 4 is almost orthogonal to the central axis line O1 of the first cylinder portion 12 (or the central axis line O2 of the inner wall defining the first insertion opening 80). In the embodiment, the central axis line of the second female connector portion 4 is almost equal to the central axis line O3 of the inner wall defining the second insertion opening 81 in the second female connector portion 4, and the central axis line of the second female connector portion 4 and the central axis line of the male connector portion 2 are also almost orthogonal to each other. Further, the central axis line of the second female connector portion 4 and the central axis line of the first female connector portion 3 are almost orthogonal to each other. That is, the connector 1 of the embodiment is a T-shaped connector called T-shaped port.

The connector 1 in the foregoing embodiment includes a main body member 90a and a lock member 90b.

The main body member 90a includes a housing 6 that internally defines a flow path 5, a first elastic valve body 7 and a second elastic valve body 8 attached to the housing 6, and an engagement member 9 fixed to the housing 6.

The housing 6 of the embodiment includes a housing trunk portion 11 that is almost circular cylindrical in outer shape, the first cylinder portion 12 that protrudes radially outward from the outer wall of the housing trunk portion 11, a second cylinder portion 13 that sandwiches the housing trunk portion 11 and protrudes radially outward from the outer wall of the housing trunk portion 11 at a position opposite to the first cylinder portion 12, and a third cylinder portion 14 that protrudes from the outer wall of the housing trunk portion 11 at a position different from the positions of the first cylinder portion 12 and the second cylinder portion 13.

The male connector portion 2 of the embodiment is formed from the first cylinder portion 12 in the housing 6 of the main body member 90a, the engagement member 9 in the main body member 90a, and the lock member 90b. The first female connector portion 3 of the embodiment is formed from the second cylinder portion 13 in the housing 6 of the main body member 90a and the first elastic valve body 7 of the main body member 90a. The second female connector portion 4 of the embodiment is formed from the third cylinder portion 14 in the housing 6 of the main body member 90a and the second elastic valve body 8 of the main body member 90a.

A trunk hollow portion 11a defined by the housing trunk portion 11, a first hollow portion 12a defined by the first cylinder portion 12, a second hollow portion 13a defined by the second cylinder portion 13, and a third hollow portion 14a defined by the third cylinder portion 14 communicate with each other. These hollow portions constitute the flow path 5 in the connector 1. The distal end side of the second hollow portion 13a in the second cylinder portion 13 constitutes the first insertion opening 80 into which the cylinder portion of a male connector portion having a predetermined shape such as that of the first cylinder portion 12 of the male connector portion 2, for example, is insertable from outside. The distal end side of the third hollow portion 14a in the third cylinder portion 14 constitutes the second insertion opening 81 into which the cylinder portion of a male connector portion having a predetermined shape different from that of the male connector portion 2 is insertable from outside.

The first elastic valve body 7 has a slit 15 that is elastically deformable to open or close when the cylinder portion of a male connector portion having a predetermined shape such as that of the first cylinder portion 12 of the male connector portion 2, for example, is inserted from outside, thereby blocking the first insertion opening 80. The second elastic valve body 8 has a slit 16 that is elastically deformable to open or close when the cylinder portion of a male connector portion having a predetermined shape different from the shape of the male connector portion 2 is inserted from the outside, thereby blocking the second insertion opening 81. The first insertion opening 80 is a space where the first elastic valve body 7 is positioned without insertion of the cylinder portion of a male connector portion, and the second insertion opening 81 is a space where the second elastic valve body 8 is positioned without insertion of the cylinder portion of a male connector portion. The flow path 5 in the connector 1 of the embodiment means the space in the housing 6 at the inner side of the first elastic valve body 7 and the second elastic valve body 8 without insertion of the cylinder portions of male connector portions into the first insertion opening 80 and the second insertion opening 81.

More specifically, the housing 6 of the embodiment includes a holder 17, and a first cap 18 and a second cap 19 supported by the holder 17. The holder 17 includes a holder main body 20 that is almost circular cylindrical in outer shape, a first holder cylinder portion 21 that is integrated with the holder main body 20 and is provided on the outer wall of the holder main body 20, and a second holder cylinder portion 22 that sandwiches the holder main body 20 and is provided on the outer wall of the holder main body 20 at a position opposite to the first holder cylinder portion 21. The first cap 18 is attached to the distal end of the second holder cylinder portion 22. The second cap 19 includes an upper cap 23 and a lower cap 24. The upper cap 23 and the lower cap 24 are attached to one end side of the circular cylindrical holder main body 20.

Accordingly, in the embodiment, the first cylinder portion 12 of the housing 6 is formed from the first holder cylinder portion 21 of the holder 17, and the first hollow portion 12a defined by the first cylinder portion 12 of the housing 6 is the hollow portion defined by the first holder cylinder portion 21. In addition, the second cylinder portion 13 of the housing 6 in the embodiment is formed from the second holder cylinder portion 22 of the holder 17 and the first cap 18, and the second hollow portion 13a defined by the second cylinder portion 13 of the housing 6 is the hollow portion defined by the second holder cylinder portion 22 and the first cap 18. Further, in the embodiment, the third cylinder portion 14 of the housing 6 is formed from the upper cap 23 and the lower cap 24 of the second cap 19, and the third hollow portion 14a defined by the third cylinder portion 14 of the housing 6 is the hollow portion defined by the upper cap 23 and the lower cap 24 of the second cap 19. In the embodiment, the housing trunk portion 11 of the housing 6 is formed from the holder main body 20, and the trunk hollow portion 11a defined by the housing trunk portion 11 is defined by the holder main body 20.

Therefore, the male connector portion 2 of the connector 1 in the embodiment is formed from the first holder cylinder portion 21 of the holder 17, the engagement member 9, and the lock member 90b. In addition, the first female connector portion 3 of the connector 1 in the embodiment is formed from the second holder cylinder portion 22 of the holder 17, the first cap 18, and the first elastic valve body 7. Further, the second female connector portion 4 of the connector 1 in the embodiment is formed from the upper cap 23 and the lower cap 24 of the second cap 19, and the second elastic valve body 8.

Examples of the material for the holder 17, the first cap 18, and the upper cap 23 and the lower cap 24 of the second cap 19 constituting the housing 6 may be, for example, various resin materials including: polyolefins such as polyethylene, polypropylene, and ethylene-propylene copolymer; ethylene-vinyl acetate copolymer (EVA); polyvinyl chloride; polyvinylidene chloride; polystyrene; polyamide; polyimide; polyamidimide; polycarbonate; poly-(4-methylpentene-1); ionomer; acrylic resin; polymethyl methacrylate; acrylonitrile-butadiene-styrene copolymer (ABS resin); acrylonitrile-styrene copolymer (AS resin); butadiene-styrene copolymer; polyesters such as polyethylene terephthalate (PET), polybutylene terephthalate (PBT), polycyclohexane terephthalate (PCT); polyether; polyether ketone (PEK); polyether ether ketone (PEEK); polyether imide; polyacetal (POM); polyphenylene oxide; modified polyphenylene oxide; polysulphone; polyether sulphone; polyphenylene sulfide; polyarylate; aromatic polyester (liquid crystal polymer); polytetrafluoroethylene, polyvinylidene fluoride, and other fluorine-based resins. In addition, a blend or a polymer alloy of one or more of the foregoing materials may be used. Alternatively, various glass materials, ceramics, or metallic materials may be used.

The first elastic valve body 7 and the second elastic valve body 8 are molded with molding dies in an elastically deformable manner. Examples of the material for the first elastic valve body 7 and the second elastic valve body 8 include, for example, various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorine rubber, and various thermal plastic elastomers such as styrene-based, polyolefin-based, polyvinyl chloride-based, polyurethane-based, polyester-based, polyamide-based, polybutadiene-based, trans polyisoprene-based, fluorine rubber-based, and chlorinated polyethylene-based elastomers. One of the foregoing materials may be singly used or two or more of them may be used in combination.

The hardness of the first elastic valve body 7 and the second elastic valve body 8 is preferably 20 to 60° (A hardness). Accordingly, the first elastic valve body 7 and the second elastic valve body 8 can have appropriate elasticity. This allows the first elastic valve body 7 and the second elastic valve body 8 to be elastically deformed at the insertion or removal of the cylinder portion of a male connector portion.

The engagement member 9 and the lock member 90b can be formed from any of the same materials as those usable for the components of the housing 6 described above.

Hereinafter, the members of the connector 1 in the embodiment and the feature units formed from the members will be described in further detail.

[Male Connector Portion 2]

First, the configuration of the male connector portion 2 of the connector 1 in the embodiment will be described in detail. As illustrated in FIGS. 1 to 4, the male connector portion 2 of the embodiment is formed from part of the main body member 90a and the lock member 90b. Specifically, the male connector portion 2 of the embodiment is formed from the first cylinder portion 12 in the housing 6 of the main body member 90a, the engagement member 9 of the main body member 90a, and the lock member 90b.

More specifically, the male connector portion 2 of the embodiment includes the first holder cylinder portion 21 that protrudes outward from the outer wall of the holder main body 20 of the holder 17, the engagement member 9 that is attached to the outer wall of the first holder cylinder portion 21 and fixed in position and has lock claws 25 that engage with a female connector portion equal in shape to the first female connector portion 3 at connection to the female connector portion, and a lock member 90b that is positioned outside the engagement member 9 in a radial direction B of the first holder cylinder portion 21 and is attached to the holder 17 in such a manner as to be movable in a central axis line direction A of the first holder cylinder portion 21 between a first position (lock position) where the amount of movement of the lock claws 25 in the outward radial direction B is limited to a predetermined amount or less and a second position (unlock position) where the movement of the lock claws 25 in the outward radial direction B is not limited to the predetermined amount or less but the amount of movement over the predetermined amount is permitted.

<First Holder Cylinder Portion 21>

Figure 5:
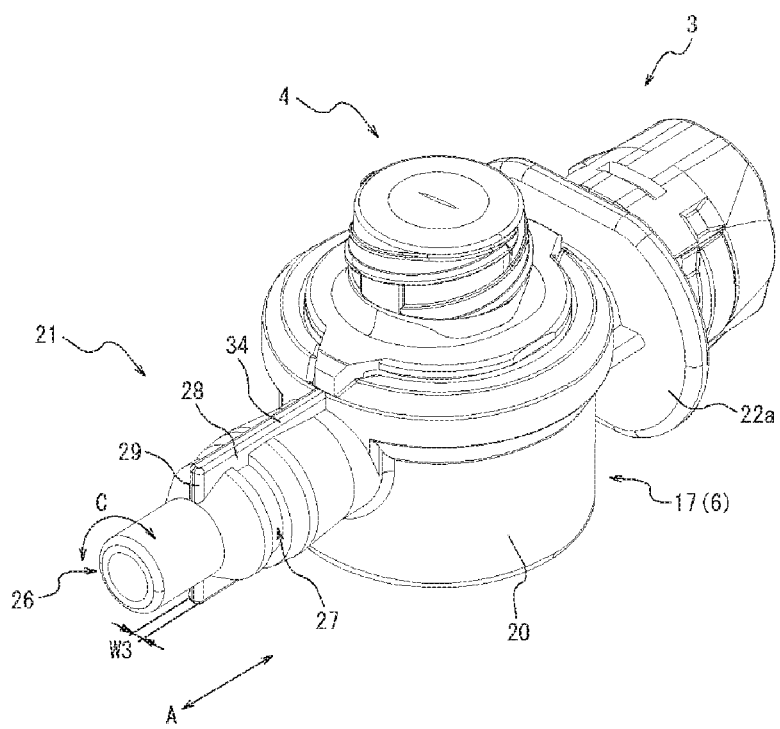
FIG. 5 is a perspective view of the connector illustrated in FIGS. 1A and 1B from which an engagement member and a lock member are removed.

FIG. 5 is a perspective view of the connector 1 from which the engagement member 9 and the lock member 90b are removed. As illustrated in FIG. 5, the first holder cylinder portion 21 is almost circular cylindrical in shape and has a distal end portion 26 insertable into and removable from an insertion opening in a female connector portion equal in shape to the first female connector portion 3. In addition, as illustrated in FIGS. 4 and 5, the first holder cylinder portion 21 has long grooves 27 extending in the circumferential direction C of the first holder cylinder portion 21 on the outer peripheral surface of a more proximal end side than the distal end portion 26 (the holder main body 20 side in the central axis line direction A). In the embodiment, the two long grooves 27 are provided at opposing positions on the transverse cross-sectional surface of the first holder cylinder portion 21 (the cross section orthogonal to the central axis line direction A). As illustrated in FIG. 5, the two long grooves 27 are separated from each other in the circumferential direction C of the first holder cylinder portion 21 by two division portions 28 intervening therebetween.

The male connector portion 2 also includes a connection inhibition portion that does not inhibit the connection to a female connector portion equal in shape to the first female connector portion 3 but inhibits the connection to a female connector portion equal in shape to the second female connector portion 4 by abutting with the female connector portion. In the embodiment, the male connector portion 2 includes the connection inhibition portion so that the male connector portion 2 cannot be connected to a female connector portion equal in shape to the second female connector portion 4. The connection inhibition portion may be designed to abut with a female connector portion equal in shape to the second female connector portion 4 at or during insertion of the male connector portion 2 into the female connector portion to inhibit the movement of the male connector portion 2 in the direction of insertion into the female connector portion (in the embodiment, the same direction as one side of the central axis line direction A).

Specifically, the outer wall of the first holder cylinder portion 21 preferably has a protrusion portion as the connection inhibition portion that protrudes in the direction of crossing over the inner periphery of one end portion of the second insertion opening 81 defined by a top plate portion 55 (see FIG. 3) of the upper cap 23 in the second female connector portion 4, or the inner wall of the member covering the first holder cylinder portion 21 (in the embodiment, the lock member 90*b* and the engagement member 9) preferably has a protrusion portion as the connection inhibition portion that protrudes and abuts with the top plate portion 55 of the upper cap 23 in the second female connector portion 4. In the configuration illustrated in FIGS. 3 and 5, the outer wall of the first holder cylinder portion 21 has a protrusion portion 29 as the connection inhibition portion protruding more outward in the radial direction B than the outer peripheral surface of the distal end portion 26, between the distal end portion 26 and the long grooves 27 and the division portions 28 in the central axis line direction A. The protrusion portion 29 does not inhibit the connection of the distal end portion 26 of the first holder cylinder portion 21 to a female connection portion equal in shape to the first female connector portion 3. However, when the distal end portion 26 of the first holder cylinder portion 21 is connecting to a female connector portion equal in shape to the second female connector portion 4, the protrusion portion 29 abuts with the upper surface (the upper surface in FIG. 3) of the top plate portion 55 of the upper cap 23 in the second female connector portion 4 to inhibit the further insertion of the distal end portion 26. The outer diameter of the distal end surface of the first holder cylinder portion 21 may be larger than the inner diameter of one end portion of the second insertion opening 81 in the second female connector portion 4, and the inner diameter of one end portion of the first insertion opening 80 may be sized such that the first holder cylinder portion 21 can be inserted therein. In such a case, the distal end surface of the first holder cylinder portion 21 abuts with the top plate portion 55 of the second female connector portion 4, and therefore the connection inhibition portion is formed from the distal end surface of the first holder cylinder portion 21.

In addition, as illustrated in FIG. 5, the outer wall of the first holder cylinder portion 21 has ribs 34 extending in the central axis line direction A at positions nearer the proximal end side than the long grooves 27 in the central axis line direction A. In the embodiment, the two ribs 34 are provided at opposing positions on the transverse cross-sectional surface of the first holder cylinder portion 21. As illustrated in FIG. 5, the division portion 28, the protrusion portion 29, and the ribs 34 of the embodiment are formed from components of an elongated rib that are connected together and extended in the central axis line direction A. Alternatively, the division portion 28, the protrusion portion 29, and the ribs 34 may be spaced in the central axis line direction A to be separately formed.

<Engagement Member 9>

Figure 6:
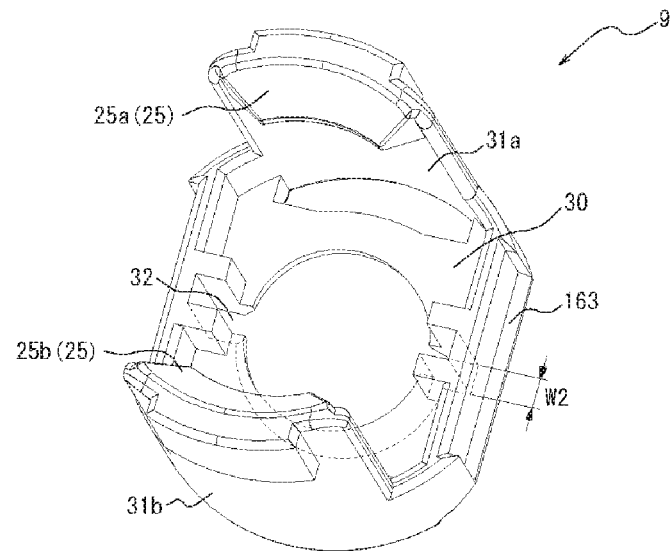
FIG. 6 is a perspective view of a single body of the engagement member in the connector illustrated in FIGS. 1A and 1B.

FIG. 6 is a perspective view of a single body of the engagement member 9. As illustrated in FIG. 6, the engagement member 9 includes a flat bottom plate portion 30 that defines an almost circular opening in the center thereof and two curved plate-like deformation portions 31*a* and 31*b* that are erected and extended from opposing outer edges of the bottom plate portion 30 in a thickness direction of the bottom plate portion 30 (the same direction as the central axis line direction A in FIG. 4).

As illustrated in FIG. 4, the first holder cylinder portion 21 penetrates the opening in the bottom plate portion 30, and the inner edge portion of the bottom plate portion 30 defining the opening fits in the long grooves 27 formed on the outer peripheral surface of the first holder cylinder portion 21. This inhibits the movement of the engagement member 9 with respect to the holder 17 in the central axis line direction A of the first holder cylinder portion 21.

In addition, as illustrated in FIG. 6, the inner edge of the bottom plate portion 30 defining the opening, that is, the inner surface of the bottom plate portion 30 defining the central opening has concave portions 32 into which the division portions 28 of the first holder cylinder portion 21 (see FIG. 5) are fitted. Therefore, when the inner edge portion of the bottom plate portion 30 is fitted in the long grooves 27 on the outer peripheral surface of the first holder cylinder portion 21, the concave portions 32 formed in the inner edge of the bottom plate portion 30 fit with the division portions 28 of the first holder cylinder portion 21 to inhibit the movement of the engagement member 9 with respect to the holder 17 in the circumferential direction C of the first holder cylinder portion 21. In the embodiment, a thickness T1 of the bottom plate portion 30 (see FIG. 4) and a width W1 of the long grooves 27 (see FIG. 4) are almost equal, and a width W2 of the concave portion 32 in the bottom plate portion 30 oriented in the circumferential direction (see FIG. 6) and a width W3 of the division portions 28 oriented in the circumferential direction (see FIG. 5) are almost equal. Accordingly, the engagement member 9 does not move with respect to the holder 17 in the central axis line direction A and the circumferential direction C of the first holder cylinder portion 21 but is fixed in position with respect to the holder 17.

As illustrated in FIG. 4, the deformation portions 31*a* and 31*b* extend along the insertion direction at a position outside the first holder cylinder portion 21 in the radial direction B of the first holder cylinder portion 21 as the first cylinder portion 12, and are capable of elastic deformation in the radial direction B. As illustrated in FIGS. 4 and 6, the deformation portions 31*a* and 31*b* curve along the circumferential direction C of the first holder cylinder portion 21, and extend from the outer edge of the bottom plate portion 30 to the upper surface side of the bottom plate portion 30 (the distal end portion 26 side of the first holder cylinder portion 21 in FIG. 4) in the central axis line direction A. The distal end portions of the deformation portions 31*a* and 31*b* (one end portion of the first holder cylinder portion 21 on the distal end portion 26 side in FIG. 4) have the lock claws 25 protruding toward the opposing deformation portion. Specifically, a lock claw 25*a* of the one deformation portion 31*a* protrudes from the distal end portion of the deformation portion 31*a* toward the opposing other deformation portion 31*b*. A lock claw 25*b* of the other deformation portion 31*b* protrudes from the distal end portion of the deformation portion 31*b* toward the opposing one deformation portion 31*a*. When the male connector portion 2 is connected to a female connector portion equal in shape to the first female connector portion 3, the lock claws 25*a* and 25*b* pass over guide inclined surfaces 51 and the like as part of the female connector portion and engage with level-difference portions 44. This will be described later in detail (see FIG. 10).

As illustrated in FIG. 4, the outer surfaces of the deformation portions 31a and 31b have abutment walls 35 formed as movement inhibition portions that abut with the lock member 90b to inhibit the movement of the lock member 90b from the second position (unlock position) to the first position (lock position) while the lock claws 25a and 25b slide on the guide inclined surfaces 51. As illustrated in FIG. 4, the abutment walls 35 are formed on outer walls of the deformation portions 31a and 31b in the outward radial direction B. The relationship in engagement between the lock member 90b and the abutment walls 35 will be described later in detail (see FIG. 10).

<Lock Member 90b>

Figure 7:
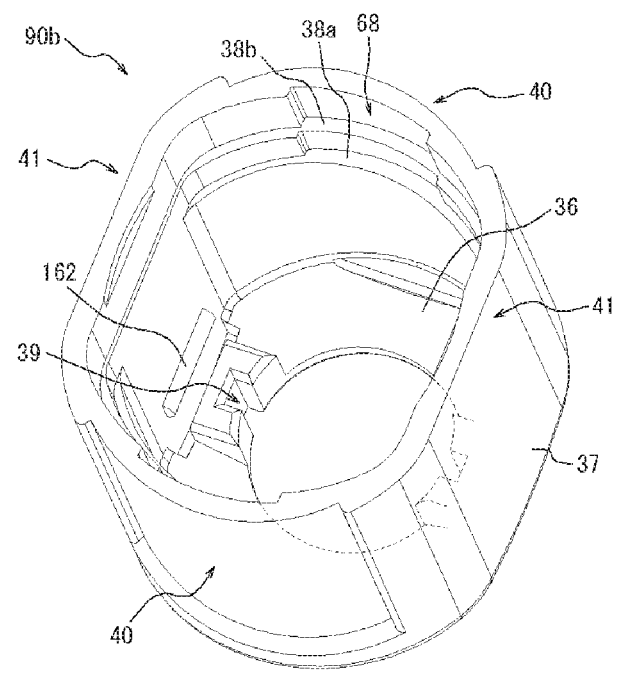
FIG. 7 is a perspective view of a single body of the lock member in the connector illustrated in FIGS. 1A and 1B.

FIG. 7 is a perspective view of a single body of the lock member 90b. As illustrated in FIG. 7, the lock member 90b includes a bottom plate portion 36 that defines an almost circular opening in the center thereof and a cylindrical cover cylinder portion 37 that is integrated and connected with the outer edge of the bottom plate portion 36. As illustrated in FIGS. 3 and 4, the first holder cylinder portion 21 penetrates the opening in the bottom plate portion 36. The cover cylinder portion 37 is positioned outside in the radial direction B of the first holder cylinder portion 21 with respect to the first holder cylinder portion 21 and the deformation portions 31a and 31b, and surrounds the first holder cylinder portion 21 and the deformation portions 31a and 31b. In other words, the deformation portions 31a and 31b of the engagement member 9 intervene between the inner wall of the cover cylinder portion 37 and the outer wall of the first holder cylinder portion 21. Further, the inner wall of the cover cylinder portion 37 is in abutment with the outer walls of the deformation portions 31a and 31b of the engagement member 9.

In the lock member 90b, the inner edge of the bottom plate portion 36, that is, the inner surface defining the opening can move in the central axis line direction A while sliding on the outer wall of the first holder cylinder portion 21. Specifically, the bottom plate portion 36 of the lock member 90b in the embodiment is movable between the outer wall of the holder main body 20 and the lower surface of the bottom plate portion 30 of the engagement member 9 (the surface on the holder main body 20 side in FIG. 4) in the central axis line direction A of the first holder cylinder portion 21. Along with the movement of the bottom plate portion 36 in the central axis line direction A, the cover cylinder portion 37 moves in the central axis line direction A while the inner surface of the cover cylinder portion 37 slides on the outer walls of the deformation portions 31a and 31b of the engagement member 9.

The cover cylinder portion 37 of the lock member 90b has an inner wall positioned outside engagement surfaces 250 of the lock claws 25 of the engagement member 9 engaging with level-difference surfaces 45a (see FIG. 1B) in the radial direction B. In order not to be unlocked from the lock claws 25, the cover cylinder portion 37 is configured to be movable in the central axis line direction A between the first position (lock position) where the amount of movement of the lock claws 25 in the outward radial direction B is limited to a predetermined amount or less and the second position (unlock position) where the amount of movement of the lock claws 25 in the outward radial direction B is not limited to a predetermined amount or less but a movement amount exceeding the predetermined amount is permitted so that the cover cylinder portion 37 can be unlocked from the lock claws 25 even when the inner wall of the cover cylinder portion 37 is not positioned outside the engagement surfaces 250 of the lock claws 25 in the radial direction B or the inner wall of the cover cylinder portion 37 is positioned outside the engagement surfaces 250 of the lock claws 25 in the radial direction B.

Specifically, in the embodiment, an example of the first position (lock position) is the position where the upper surface of the bottom plate portion 36 (the surface on the distal end portion 26 side of the first holder cylinder portion 21 in FIG. 4) abuts with the lower surface of the bottom plate portion 30 of the engagement member 9. The inner wall of the cover cylinder portion 37 of the lock member 90b in the first position abuts with the outer walls of the deformation portions 31a and 31b outside the radial direction B outside the lock claws 25 in the radial direction B.

Meanwhile, in the embodiment, an example of the second position (unlock position) is the position where the lower surface of the bottom plate portion 36 (the surface positioned on the holder main body 20 side in FIG. 4) abuts with the outer peripheral surface of the holder main body 20. The inner wall of the cover cylinder portion 37 of the lock member 90b in the second position does not abut with the outer walls of the deformation portions 31a and 31b outside the lock claws 25 in the radial direction B.

That is, when the lock member 90b is in the second position (unlock position), the distal end portions of the deformation portions 31a and 31b with the lock claws 25a and 25b are prone to elastically deform and expand outward in the radial direction B. Meanwhile, when the lock member 90b is in the first position (lock position), as compared to the state in the second position, the distal end portions of the deformation portions 31a and 31b are less prone to elastically deform and expand outward in the radial direction. In the male connector portion 2 of the embodiment, the position of the lock member 90b can be switched between the first position and the second position. This ensures operability in connecting the male connector portion 2 to a female connector portions equal in shape to the first female connector portion 3 and improves the safety after the connection. This will be described later in detail (see FIG. 10).

Further, as illustrated in FIGS. 4 and 7, the inner surface of the cover cylinder portion 37 has first level-difference surfaces 38a that abut with the abutment walls 35 of the engagement member 9 (see FIG. 4) in the first position (lock position). As illustrated in FIG. 4, the first level-difference surfaces 38a face the distal end of the first holder cylinder portion 21 in the central axis line direction A. In the lock member 90b of the embodiment, the upper surface of the bottom plate portion 36 abuts with the lower surface of the bottom plate portion 30 of the engagement member 9, and the first level-difference surfaces 38a of the cover cylinder portion 37 abut with the abutment walls 35 formed on the outer walls of the deformation portions 31a and 31b, thereby suppressing falling of the cover cylinder portion 37 from the first holder cylinder portion 21. In the embodiment, the falling of the cover cylinder portion 37 from the first holder cylinder portion 21 is suppressed by both the abutment between the abutment walls 35 of the engagement member 9 and the first level-difference surfaces 38a of the lock member 90b and the abutment between the lower surface of the bottom plate portion 30 of the engagement member 9 and the upper surface of the bottom plate portion 36 of the lock member 90b. However, the present invention is not limited to this configuration. Rather, the falling of the cover cylinder portion 37 may be suppressed by either one of them.

Further, as illustrated in FIGS. 4 and 7, the inner surface of the cover cylinder portion 37 has second level-difference surfaces 38b as abutment portions that abut with the abutment walls 35 (see FIG. 4) of the engagement member 9 under a certain condition to inhibit the movement of the lock member 90b from the second position (unlock position) to the first position (lock position). The second level-difference surfaces 38b are positioned nearer the distal end side of the first holder cylinder portion 21 than the first level-difference surfaces 38a in the central axis line direction A. The second level-difference surfaces 38b face the distal end side of the first holder cylinder portion 21 in the central axis line direction A as with the first level-difference surfaces 38a. The engagement relationship between the abutment walls 35 and the second level-difference surfaces 38b will be described later in detail (see FIG. 10).

As illustrated in FIGS. 3 and 4, the bottom plate portion 36 of the embodiment is tapered such that the inner edge portion of the bottom plate portion 36 is narrower than the outer edge portion of the bottom plate portion 36. In addition, as illustrated in FIG. 7, the inner edge of the bottom plate portion 36 defining the opening, that is, the inner surface of the bottom plate portion 36 defining the central opening has concave portions 39 into which the ribs 34 of the first holder cylinder portion 21 (see FIG. 5) fit. The lock member 90b is attached to the first holder cylinder portion 21 such that the concave portions 39 formed in the bottom plate portion 36 fit to the ribs 34 in the first holder cylinder portion 21, thereby to inhibit the movement of the lock member 90b in the circumferential direction C with respect to the first holder cylinder portion 21.

Further, as illustrated in FIG. 7, the cover cylinder portion 37 of the lock member 90b is formed from opposing curved portions 40 and opposing flat plate portions 41 that connect the opposing curved portions 40. In addition, the deformation portions 31a and 31b of the engagement member 9 are arranged to abut with the inner surfaces of the curved portions 40 of the cover cylinder portion 37 and extend along the curved portion 40. Therefore, when an attempt to rotate the lock member 90b in the circumferential direction C is made, the both end portions of the deformation portions 31a and 31b of the engagement member 9 in the circumferential direction C and the inner surfaces of the flat plate portions 41 of the cover cylinder portion 37 abut and interfere with each other to inhibit the rotation of the lock member 90b in the circumferential direction C.

In this way, the lock member 90b of the embodiment is configured not to rotate in the circumferential direction C with respect to the first holder cylinder portion 21 and the engagement member 9 by both fitting the concave portions 39 in the bottom plate portion 36 to the ribs 34 in the first holder cylinder portion 21 and bringing the both ends of the deformation portions 31a and 31b in the engagement member 9 oriented in the circumferential direction C into abutment and interference with the inner surfaces of the flat plate portions 41 of the cover cylinder portion 37. However, the present invention is not limited to this configuration. For example, the rotation of the lock member 90b in the circumferential direction C with respect to the first holder cylinder portion 21 and the engagement member 9 may be inhibited only by either one of the foregoing configurations.

The first level-difference surfaces 38a and the second level-difference surfaces 38b are provided on the inner surfaces of the curved portions 40 of the cover cylinder portion 37. The distance between the opposing curved portions 40 is first longer via the first level-difference surfaces 38a toward the distal end side of the first holder cylinder portion 21 and then is further longer via the second level-difference surfaces 38b. That is, the inner surfaces of the curved portions 40 are widened stepwise outward in the radial direction B via the first level-difference surfaces 38a and the second level-difference surfaces 38b in increasing proximity to the distal end side of the first holder cylinder portion 21. The second level-difference surfaces 38b and a distal-end widened portion of the inner surface widened via the second level-difference surfaces 38b form a reception portion 68 that can receive at least part of the deformation portions 31a and 31b elastically deformed outward in the radial direction B. When the deformation portions 31a and 31b are elastically deformed with the distal ends widened outward in the radial direction B while the lock member 90b is in the second position (unlock position), at least part of the deformation portions 31a and 31b enters the reception portion 68. In other words, the second level-difference surfaces 38b as the abutment portions described above are provided in the reception portion 68.

[First Female Connector Portion 3]

Next, the first female connector portion 3 connectable to a male connector portion equal in shape to the male connector portion 2 will be further described in detail. The first female connector portion 3 of the embodiment includes the second holder cylinder portion 22 that protrudes outward from the outer wall of the holder main body 20 in the holder 17, the first cap 18 that is attached to the distal end of the second holder cylinder portion 22, and the first elastic valve body 7 that is positioned within the first insertion opening 80 defined by the second holder cylinder portion 22 and the first cap 18.

<First Elastic Valve Body 7>

Figure 8A:
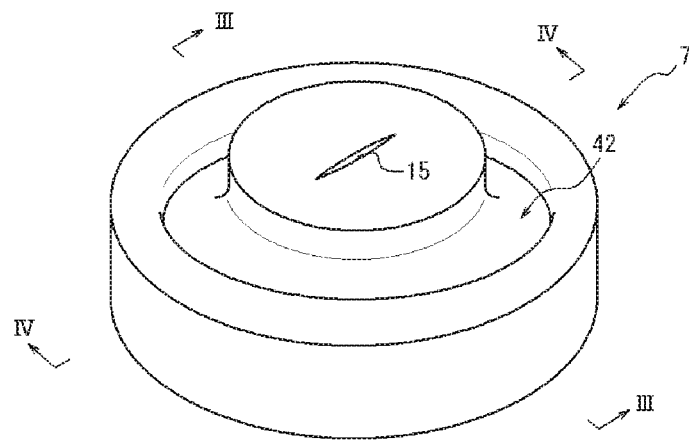
FIG. 8A is a perspective view of a single body of a first elastic valve body in the connector illustrated in FIGS. 1A and 1B.
Figure 8B:
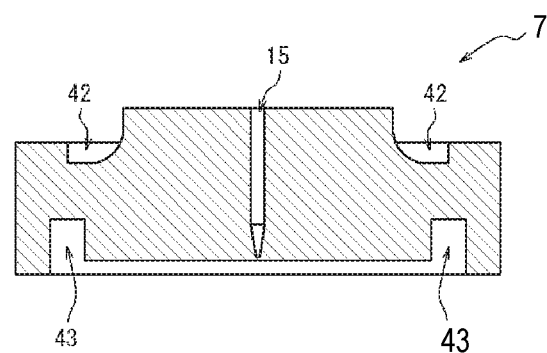
FIG. 8B is a cross-sectional view of FIG. 8A taken along line III-III.
Figure 8C:
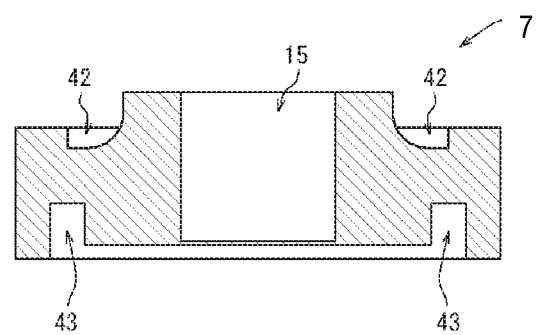
FIG. 8C is a cross-sectional view of FIG. 8A taken along line IV-IV.

FIG. 8A is a perspective view of a single body of the first elastic valve body 7, FIG. 8B is a cross-sectional view of FIG. 8A taken along line III-III, and FIG. 8C is a cross-sectional view of FIG. 8A taken along line IV-IV. As illustrated in FIG. 8, the first elastic valve body 7 is a circular flat elastic valve body. The first elastic valve body 7 has the straight-line slit 15 described above in the central region of the upper surface (the upper surface in FIG. 8 and the left surface in FIGS. 3 and 4) and has an upper annular groove 42 in the outer peripheral region on the periphery of the central region. The first elastic valve body 7 has also a lower annular groove 43 in the outer peripheral region of the lower surface opposite to the upper surface. The slit 15 is not formed in the central region of the lower surface. At the time of first insertion of a male connector portion, for example, the portion of the first elastic valve body 7 between the distal end of the slit 15 formed in the upper surface and the central region in the lower surface is torn down to let the slit 15 communicate from the upper surface to the lower surface. The step of letting the slit 15 penetrate the lower surface can be executed as part of the manufacturing process after completion of the molding of the first elastic valve body 7.

<Second Holder Cylinder Portion 22>

Figure 9:
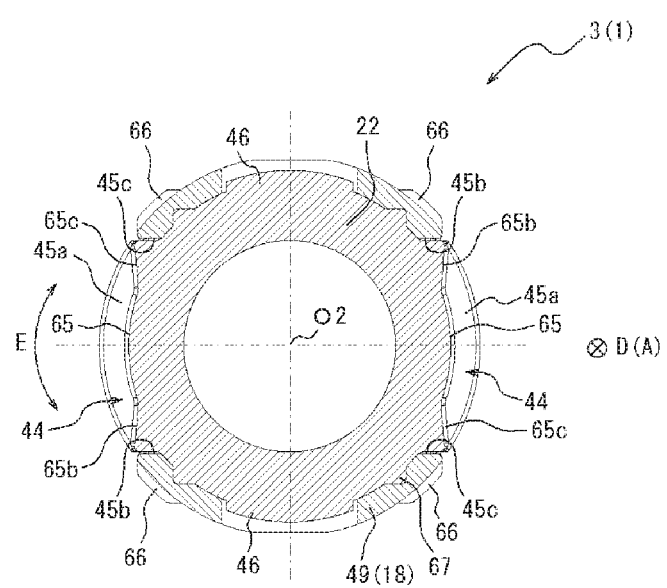
FIG. 9 is a cross-sectional view of FIG. 2B taken along line V-V.

FIG. 9 is a cross-sectional view of FIG. 2B taken along line V-V. As illustrated in FIGS. 1 and 9, the outer wall of the second holder cylinder portion 22 has the level-difference portions 44 in which the lock claws 25 of the engagement member 9 get caught in and engage with a male connector portion equal in shape to the male connector portion 2 at the time of connection. In addition, as illustrated in FIG. 1B, the level-difference portions 44 of the embodiment are formed at positions corresponding to the two lock claws 25a and 25b of the male connector portion 2 (two right and left positions on the outer wall of the second holder cylinder portion 22 in FIG. 1B). Further, as illustrated in FIG. 9, the level-difference portions 44 of the embodiment include level-difference surfaces 45a that are positioned on the distal end side of the second holder cylinder portion 22 oriented in a central axis line direction D of the second holder cylinder portion 22 (the same direction as the central axis line direction A of the first holder cylinder portion 21 and the central axis line direction of the inner wall defining the first insertion opening 80 in the embodiment), and extend in a direction orthogonal to the central axis line direction D. The level-difference portions 44 in the second holder cylinder portion 22 are adjacent to the level-difference surfaces 45b and 45c formed by a first cap 18 described later in the circumferential direction E of the second holder cylinder portion 22.

Each of the level-difference portions 44 of the second holder cylinder portion 22 has a bottom portion 65 continued from the level-difference surface 45a, where the distal end side of the second holder cylinder portion 22 is surrounded by the level-difference surface 45a, one side of the second holder cylinder portion 22 in the circumferential direction E is surrounded by the level-difference surface 45b, and the other side of the second holder cylinder portion 22 in the circumferential direction E is surrounded by the level-difference surface 45c. As illustrated in FIG. 9, the both ends of the bottom portion 65 in the circumferential direction E are formed by connection slopes 65b and 65c that lessen sharp level differences between the level-difference surfaces 45b and 45c. More specifically, the connection slopes 65b and 65c are planar slopes with gradual increase in the radial distance from the central axis line O2 of the second holder cylinder portion 22 with increasing proximity to the outside of the bottom portion 65 in the circumferential direction E. With the connection slopes 65b and 65c, the bottom portions 65 connect smoothly to the outer peripheral surfaces of side wall portions 49 described later of the first cap 18 without a large level difference. The engagement relationship between the lock claws 25 of the male connector portion 2 and the level-difference surfaces 45a in the level-difference portions 44 of the second holder cylinder portion 22, and the engagement relationship between the lock claws 25 and the bottom portions 65 of the level-difference portions 44 and the side wall portions 49 of the first cap 18 will be described later in detail (see FIG. 10). For the convenience of description, the level-difference surfaces 45a in the level-difference portions 44 of the second holder cylinder portion 22 will be referred to as "first level-difference surfaces 45a", and the level-difference surfaces 45b and 45c of the first cap 18 will be referred to as "second level-difference surfaces 45b" and "third level-difference surfaces 45c".

As illustrated in FIGS. 1 to 5, the second holder cylinder portion 22 includes an annular flange portion 22a that protrudes outward in the radial direction at a position nearer the proximal end than the level-difference portions 44. In addition, as illustrated in FIGS. 1A, 3, and 9, the outer wall of the second holder cylinder portion 22 has projection portions 46 that fit into the openings in the side wall portions 49 of the first cap 18 described later to fix the position of the first cap 18 with respect to the second holder cylinder portion 22. As illustrated in FIG. 9, the projection portions 46 of the embodiment are formed in positions almost equal to the positions of the level-difference portions 44 in the central axis line direction D of the second holder cylinder portion 22 and in positions different from the positions of the level-difference portion 44 in the circumferential direction E.

Further, as illustrated in FIG. 9, besides the projection portions 46, the outer surface of the second holder cylinder portion 22 has convex portions 67 that protrude outward in the radial direction to fit into concave portions on the inner surfaces of the side wall portions 49 of the first cap 18 described later.

Further, as illustrated in FIG. 4, the second holder cylinder portion 22 has at the distal end portion an annular lock projection 47 that compresses and sandwiches the first elastic valve body 7 in conjunction with the first cap 18. Specifically, the lock projection 47 enters the lower annular groove 43 (see FIGS. 8B and 8C) in the first elastic valve body 7 to compress and sandwich the first elastic valve body 7 in conjunction with a lock projection 50 described later in the first cap 18.

<First Cap 18>

As illustrated in FIGS. 1, 3, and 4, the first cap 18 includes a top plate portion 48 defining an almost circular opening in the center and an almost circular cylindrical side wall portion 49 that is continued from the outer edge of the top plate portion 48.

The top plate portion 48 defines one end portion of the first insertion opening 80 into which a male connector portion equal in shape to the male connector portion 2 is insertable, and has the annular lock projection 50 that protrudes toward the inside of the connector 1 oriented in the central axis line direction D at the lower end of the inner peripheral surface defining the one end portion of the first insertion opening 80 (the right end of the inner peripheral surface in the cross-sectional views of FIGS. 3 and 4). The lock projection 50 enters the upper annular groove 42 in the first elastic valve body 7 (see FIG. 8) and compresses and sandwiches the first elastic valve body 7 in conjunction with the lock projection 47 in the second holder cylinder portion 22 that enters the lower annular groove 43 in the first elastic valve body 7 (see FIGS. 8B and 8C).

The side wall portion 49 is almost circular cylindrical in shape and defines the first insertion opening 80 in conjunction with the top plate portion 48. The other end of the side wall portion 49 opposite to the one end connected to the top plate portion 48 is attached to the second holder cylinder portion 22. Accordingly, the first cap 18 is supported by the second holder cylinder portion 22. The first cap 18 of the embodiment is fixed in position with respect to the second holder cylinder portion 22 by the projection portions 46 fitted into the openings in the side wall portions 49 and the convex portions 67 into the concave portions on the inner surfaces of the side wall portions 49. In addition to this fixing means, the first cap 18 may be attached to the second holder cylinder portion 22 by ultrasonic bonding, for example.

As illustrated in FIGS. 1 to 4, the outer wall of the side wall portion 49 of the first cap 18 has guide inclined surfaces 51 that are inclined with respect to the central axis line O2 and guides the lock claws 25a and 25b of the deformation portions 31a and 31b in the engagement member 9 of the male connector portion 2 to the level-difference portions 44 of the second holder cylinder portion 22 at the time of connection to a male connector portion equal in shape to the male connector portion 2. Specifically, when a male connector portion equal in shape to the male connector portion 2 is connected to the first female connector portion 3, the first holder cylinder portion 21 is inserted into the first insertion opening 80 while elastically deforming the first elastic valve body 7, and the lock claws 25a and 25b of the deformation portions 31a and 31b slide on the guide inclined surfaces 51, and the distal end portions of the deformation portions 31a and 31b are guided to the level-difference portions 44 along the guide inclined surfaces 51 and part of the second holder cylinder portion 22 extending continuously from the guide inclined surfaces 51 while the distal end portions are elastically deformed and expended outward in the radial direction B of the first holder cylinder portion 21 (outward in the radial direction F of the second holder cylinder portion 22 in the embodiment).

When the lock claws 25a and 25b reach the level-difference portions 44 of the second holder cylinder portion 22, the lock claws 25a and 25b move inward in the radial direction B by resilience, enter the level-difference portions 44, and get caught and engage with the first level-difference surfaces 45a of the level-difference portions 44. Accordingly, the connection of the male connector portion equal in shape to the male connector portion 2 and the first female connector portion 3 is completed. This connecting action will be described later in detail (see FIG. 10).

As illustrated in FIGS. 1 to 4, the first cap 18 is attached to the second holder cylinder portion 22 such that the side wall portions 49 cover the outer wall of the distal end portion of the second holder cylinder portion 22. The side wall portions 49 extend up to the positions adjacent to the level-difference portions 44 of the second holder cylinder portion 22 in the circumferential direction E. Accordingly, the side wall portions 49 form the second level-difference surfaces 45b and the third level-difference surfaces 45c on the both sides of the level-difference portions 44 in the circumferential direction E.

Further, as illustrated in FIGS. 1, 2, 9, and others, the side wall portions 49 have on the outer surface, protrusion portions 66 that protrude outward in the radial direction F at positions adjacent to the level-difference portions 44 in the circumferential direction E and nearer the distal end side (the top plate portion 48 side) of the second holder cylinder portion 22 than the level-difference portions 44 in the central axis line direction D. The lock claws 25 that enters the level-difference portions 44 can slide on the connection slopes 65b or 65c and come out of the level-difference portions 44 by rotating the lock claws 25 in the circumferential direction E with respect to the second holder cylinder portion 22 and the first cap 18. However, the lock claws 25 having come out of the level-difference portions 44 cannot move in the direction of separating from the first female connector portion 3 in the central axis line direction D due to the presence of the protrusion portions 66. That is, the lock claws 25 having come out of the level-difference portions 44 abut with the protrusion portions 66 and cannot be separated from the first female connector portion 3 even if an attempt is made to move the lock claws 25 in the direction of separating from the first female connector portion 3 in the central axis line direction D.

Therefore, to move the lock claws 25 in the direction of separating from the first female connector portion 3 in the central axis line direction D, the lock claws 25 need to be rotated in the circumferential direction E for a predetermined distance or more (at a predetermined central angle or more around the central axis line O2) with respect to the second holder cylinder portion 22 and the first cap 18 to bring the lock claws 25 and the protrusion portions 66 into a positional relationship with no overlap in the central axis line direction D. Establishing this positional relationship makes it possible to move the lock claws 25 in no abutment with the protrusion portions 66 in the direction of separating from the first female connector portion 3 in the central axis line direction D.

That is, with the protrusion portions 66, the connector 1 of the embodiment can inhibit the lock claws 25 that has entered the level-difference portions 44 from moving in the direction of separating from the first female connector portion 3 in the central axis line direction D even if the lock claws 25 has come out of the level-difference portions 44 accidentally or unintentionally, thereby suppressing the separation of the male connector portion equal in shape to the male connector portion 2 from the first female connector portion 3 accidentally or unintentionally. In other words, to disconnect intentionally the male connector portion equal in shape to the male connector portion 2 and the first female connector portion 3 in the state where the male connector portion and the first female connector portion 3 are connected, the presence of the protrusion portions 66 causes the user to rotate the lock claws 25 by a predetermined distance or more in the circumferential direction E with respect to the second holder cylinder portion 22 and the first cap 18, thereby suppressing the occurrence of accidental or unintentional disconnection.

The protrusion portion 66 of the embodiment is provided on both sides of the level-difference portion 44 in the circumferential direction E. Alternatively, the protrusion portion 66 may be provided on either of the sides. However, it is preferred that the protrusion portions 66 inhibit the movement of the lock claws 25 toward the distal end of the second holder cylinder portion 22 even if the lock claws 25 are rotated to either one side with respect to the second holder cylinder portion 22 and the first cap 18 in the circumferential direction E. When the protrusion portions 66 are provided on the both sides of the level-difference portion 44 in the circumferential direction E as in the embodiment or there exists a plurality of level-difference portions 44, for example, it is preferred that one protrusion portion 66 is provided on one level-difference portion 44 on one side in the circumferential direction E and another protrusion portion 66 is provided on another level-difference portion 44 on the other side in the circumferential direction E.

As described above, the guide inclined surfaces 51 of the embodiment are formed at two opposing places on the outer wall of the side wall portion 49 corresponding to the positions of the lock claws 25a and 25b of the male connector portion 2 oriented in the circumferential direction of the first holder cylinder portion 21. However, the present invention is not limited to this configuration. The guide inclined surfaces 51 can be designed as appropriate according to the circumferential positions and number of the lock claws of the male connector portion shaped to be connectable to the first female connector portion 3.

[Second Female Connector Portion 4]

Next, the second female connector portion 4 will be described. The second female connector portion 4 of the embodiment includes the upper cap 23, the lower cap 24, and the second elastic valve body 8. The second female connector portion 4 of the embodiment is not connectable to a male connector portion equal in shape to the male connector portion 2 but is shaped to be connectable to a lock-type male connector portion prescribed in ISO594.

<Second Elastic Valve Body 8>

The second elastic valve body 8 is a circular flat valve body that has a straight-line slit 16 in the center of the upper surface (the upper surface in FIG. 3). The slit 16 is molded by a molding die and does not penetrate the lower surface at the time of molding but penetrates the lower surface at the first insertion of the male connector portion after the molding, for example. The step of letting the slit 16 penetrate the lower surface can be executed as part of the manufacturing process after completion of the molding.

The second elastic valve body 8 has an upper annular groove in the outer peripheral region of the upper surface.

The second elastic valve body 8 has also a lower annular groove in the outer peripheral region of the lower surface.

<Upper Cap 23>

As illustrated in FIG. 3, the upper cap 23 includes a top plate portion 55, an almost circular cylindrical cylinder portion 56 that is connected to the outer edge of the top plate portion 55, and a flange portion 57 that is connected to the other end of the cylinder portion 56 opposite to the one end connected to the top plate portion 55. As illustrated in FIG. 3, the top plate portion 55 defines one end portion of the second insertion opening 81 into which a male connector portion of a predetermined shape is insertable. The lower end of the inner peripheral surface 55a of the top plate portion 55 (one end of the lower side of the inner peripheral surface in FIG. 3) defining the one end portion of the second insertion opening 81 has an annular lock projection that protrudes toward the inside of the connector 1 oriented in a central axis line direction G of the inner wall defining the second insertion opening 81 (the direction orthogonal to the central axis line directions A and D and equal to the central axis line direction of the cylinder portion 56 in the embodiment). The lock projection enters the upper annular groove in the second elastic valve body 8, and compresses and sandwiches the second elastic valve body 8 in conjunction with the lock projection in the lower cap 24 that enters the lower annular groove in the second elastic valve body 8.

In addition, as illustrated in FIG. 3, the inner peripheral surface 55a of the top plate portion 55 contacts the upper surface of the second elastic valve body 8 without connection to a male connector portion, and contacts an ISO594-prescribed male connector portion with connection to the male connector portion. Specifically, the central region on the upper surface of the second elastic valve body 8 fits into the space (the one end portion of the second insertion opening 81) surrounded by the inner peripheral surface 55a of the top plate portion 55 without connection to a male connector portion, and the outer peripheral surface of a male lure of an ISO-prescribed male connector portion contacts the inner peripheral surface 55a of the top plate portion 55 with connection to the male connector portion, and the male lure and the top plate portion 55 fit together. In the embodiment, the inner peripheral surface 55a of the top plate portion 55 is circular cylindrical in parallel to the central axis line direction G. Alternatively, the inner peripheral surface 55a of the top plate portion 55 may be tapered with gradual decrease in inner diameter with increasing proximity to the inside of the connector 1 in the central axis line direction G according to the outer shape of a male connector portion. In addition, in the embodiment, with connection to a male connector portion, the male connector portion fits to the upper cap 23 by the inner peripheral surface 55a of the circular cylindrical top plate portion 55. However, the present invention is not limited to this configuration. Rather, with connection to a male connector portion, the male connector portion may not contact the inner peripheral surface 55a of the top plate portion 55.

The outer peripheral surface of the cylinder portion 56 has a male screw portion 59 to screw into an ISO594-prescribed lock connector. The flange portion 57 is a portion molded integrally with the cylinder portion 56. When the flange portion 57 engages with the holder main body 20, the upper cap 23 is held in the holder 17.

<Lower Cap 24>

As illustrated in FIG. 3, the lower cap 24 includes an almost circular cylindrical cylinder portion 60 and a flange portion 61 connected to one end of the cylinder portion 60. The other end side of the cylinder portion 60 has an annular lock projection that protrudes toward the connector 1 in the central axis line direction G (the upward direction in FIG. 3) and enters the lower annular groove in the second elastic valve body 8 to compress the second elastic valve body 8, and sandwich the second elastic valve body 8 in conjunction with the lock projection of the upper cap 23. In this way, the second elastic valve body 8 is compressed and sandwiched in a sandwich portion formed from the lock projection of the upper cap 23 and the lock projection of the lower cap 24, and is fixed in position within the third hollow portion 14a, specifically, within the second insertion opening 81.

The lower cap 24 is held by the upper cap 23 by ultrasonic-bonding to the inner surface of the cylinder portion 56 of the upper cap 23 and/or the lower surface of the flange portion 57 (the lower surface in FIG. 3), and is fixed in position by holding the flange portion 61 of the lower cap 24 in the holder 17.

The holder 17 of the embodiment supports both the upper cap 23 and the lower cap 24 by direct contact with the two caps. Alternatively, for example, the holder 17 may contact directly only the lower cap 24 without contact with the upper cap 23 so that the upper cap 23 contacts the lower cap 24 and is supported by the lower cap 24. That is, the holder 17 may contact directly either one of the upper cap 23 and the lower cap 24 and support the one without direct contact with the other. The members to contact directly each other are preferably bonded by ultrasonic bonding, for example.

In addition, in the embodiment, the upper cap 23 and the lower cap 24 sandwich the second elastic valve body 8 therebetween to hold the second elastic valve body 8 within the second insertion opening 81. Alternatively, for example, the second elastic valve body 8 may be compressed and sandwiched between a holder formed integrally by the holder 17 in the embodiment and the lower cap 24 and an upper cap as in the embodiment. That is, the housing 6 of the connector 1 in the embodiment is formed from the holder 17, the first cap 18, and the upper cap 23 and the lower cap 24 of the second cap 19. However, more than one of these members may be integrally formed, and one of these members may be formed from a combination of two or more members.

[Connection Between the Male Connector Portion 2 and the Female Connector Portion 3' Equal in Shape to the First Female Connector Portion 3]

Next, the operations of components for connecting the male connector portion 2 of the connector 1 to the female connector portion 3' equal in shape to the first female connector portion 3 of another medical device 300 will be described. The female connector portion 3' is equal in configuration to the first female connector portion 3 described above, and thus the components of the female connector portion 3' will be described using the same reference signs to those of the first female connector portion 3.

Figure 10A:
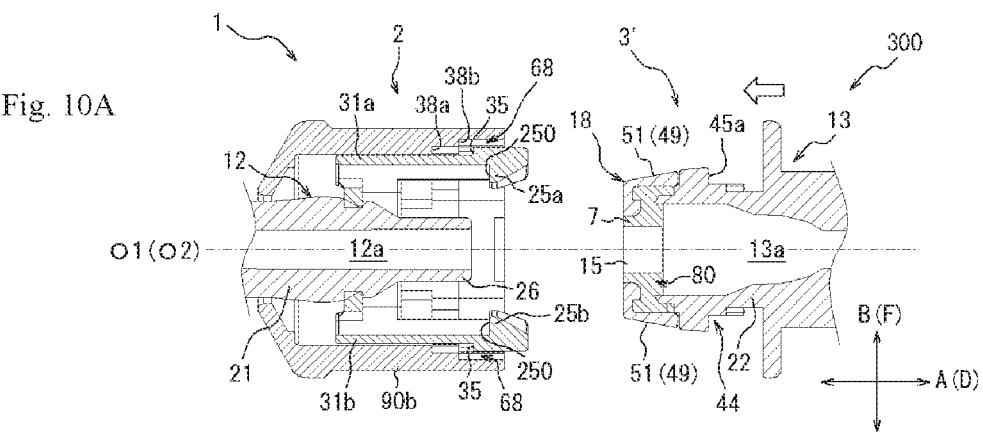
FIGS. 10A to 10C are views illustrating changes in state of connection between the connector illustrated in FIGS. 1A and 1B and a medical device including a female connector portion equal in shape to a first female connector portion of the connector illustrated in FIG. 1.
Figure 10B:
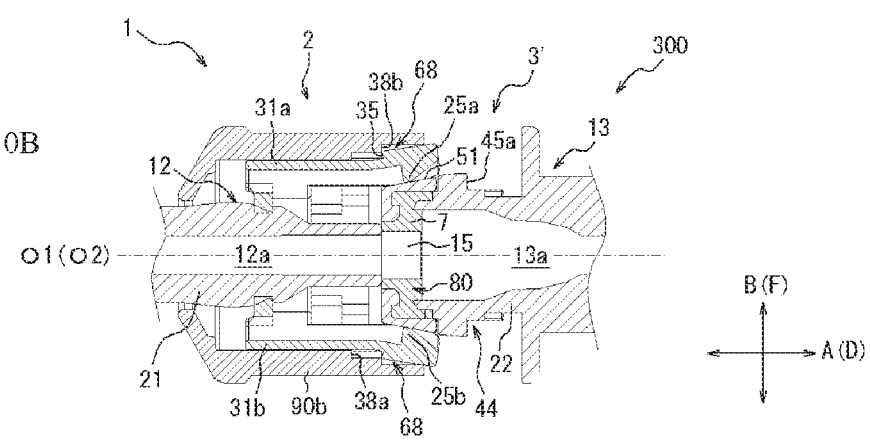
Figure 10C:
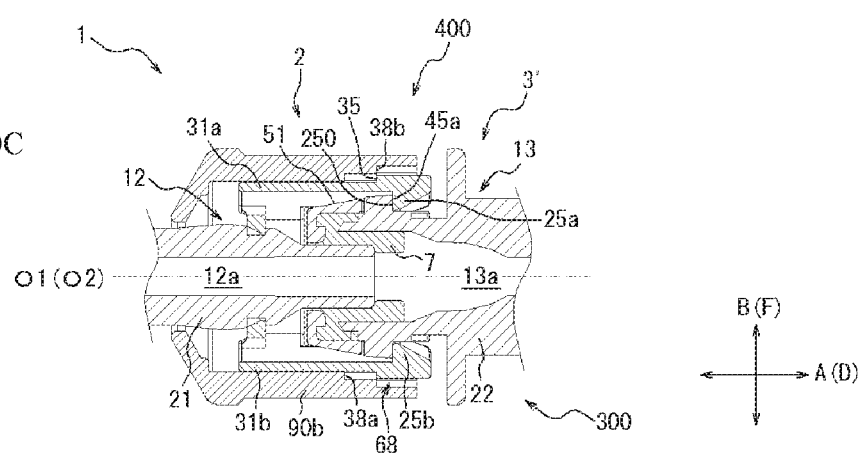

FIGS. 10A to 10C are views illustrating changes in the state of connection of the connector 1 of the embodiment to the medical device 300 including the female connector portion 3' equal in shape to the first female connector portion 3. Specifically, FIG. 10A illustrates the state before the connection of the male connector portion 2 of the connector 1 and the female connector portion 3' of the medical device 300, that is, the state in which the male connector portion 2 of the connector 1 and the female connector portion 3' of the medical device 300 are separated from each other. FIG. 10B illustrates the state in which the male connector portion 2 of the connector 1 and the female connector portion 3' of the medical device 300 are being connected. FIG. 10C illustrates the state in which the male connector portion 2 of the connector 1 and the female connector portion 3' of the medical device 300 are completely connected.

To connect the male connector portion 2 of the connector 1 and the female connector portion 3' of the medical device 300, the male connector portion 2 and the female connector portion 3' are brought close to each other in the central axis line direction A (equal to the central axis line direction D) while the central axis line O1 of the first holder cylinder portion 21 of the male connector portion 2 and the central axis line O2 of the second holder cylinder portion 22 of the female connector portion 3' are approximately aligned to each other. FIG. 10A illustrates the example in which the female connector portion 3' of the medical device 300 is moved close to the male connector portion 2 of the connector 1 in the direction indicated by a hollow arrow. Alternatively, the male connector portion 2 of the connector 1 may be moved close to the female connector portion 3' of the medical device 300 or the two may be moved close to each other.

When the male connector portion 2 of the connector 1 connects to the female connector portion 3' of the medical device 300, the lock member 90*b* of the male connector portion 2 is in the second position (unlock position) so that the lock claws 25*a* and 25*b* as lock portions of the engagement member 9 are deformable outward in the radial direction B. To connect the male connector portion 2 of the connector 1 to the female connector portion 3' of the medical device 300, the user such as medical personnel brings the male connector portion 2 and the female connector portion 3' close to each other while grasping the lock member 90*b* in the second position.

In the state of FIG. 10A, the abutment walls 35 provided on the deformation portions 31*a* and 31*b* of the engagement member 9 and facing the proximal end side of the first holder cylinder portion 21 are not opposed to the second level-difference surfaces 38*b* of the lock member 90*b* in the central axis line direction A.

As illustrated in FIG. 10B, when the male connector portion 2 and the female connector portion 3' are brought close to each other, the lock claws 25*a* and 25*b* of the engagement member 9 slide on the guide inclined surfaces 51 of the side wall portions 49 of the first cap 18 in the female connector portion 3', and the deformation portions 31*a* and 31*b* elastically deform to move the lock claws 25*a* and 25*b* outward in the radial direction B (equal to outward in the radial direction F). At that time, the abutment walls 35 of the engagement member 9 are opposed to the second level-difference surfaces 38*b* of the lock member 90*b* in the central axis line direction A. Accordingly, in the state of FIG. 10B, even if an attempt is made to move the lock member 90*b* from the second position (unlock position) to the first position (lock position), the abutment walls 35 of the engagement member 9 abut with the second level-difference surfaces 38*b* of the lock member 90*b* so that the lock member 90*b* cannot move to the first position.

Therefore, it is possible to suppress the movement of the lock member 90*b* to the first position while the lock claws 25*a* and 25*b* of the engagement member 9 pass over the guide inclined surfaces 51 of the female connector portion 3'.

When the male connector portion 2 and the female connector portion 3' are further brought close to each other in the central axis line direction A from the state of FIG. 10B, the distal end portion 26 of the first holder cylinder portion 21 of the male connector portion 2 pushes the second elastic valve body 8 of the female connector portion 3' into the female connector portion 3' so that the second elastic valve body 8 is inserted into the first insertion opening 80 while pressing the slit 15 apart.

Then, after the lock claws 25*a* and 25*b* have passed over the guide inclined surfaces 51 and the partial outer wall of the second holder cylinder portion 22 extending and continuing from the guide inclined surfaces 51, the lock claws 25*a* and 25*b* move inward in the radial direction B by resilience. Then, the engagement surfaces 250 of the lock claws 25*a* and 25*b* engage with the first level-difference surfaces 45*a* as illustrated in FIG. 10C. Accordingly, the female connector portion 3' is locked by the lock claws 25*a* and 25*b* to complete the connection between the male connector portion 2 and the female connector portion 3', thereby forming a connector connected body 400 in which the female connector portion 3' cannot be pulled out of the male connector portion 2.

In the state illustrated in FIG. 10C, even when an attempt is made to move the male connector portion 2 distant from the female connector portion 3' in the central axis line direction A, the engagement surfaces 250 of the lock claws 25 of the male connector portion 2 abut with the first level-difference surfaces 45*a* of the level-difference portions 44 of the female connector portion 3' to suppress the falling of the male connector portion 2 from the first holder cylinder portion 21. Accordingly, even if the connectors 1 and the medical device 300 are moved to be distant from each other in the central axis line direction A, no disconnection can be easily done. That is, the male connector portion 2 and the female connector portion 3' of the embodiment do not require the engagement of a male screw portion and a female screw portion in lock-type connectors. The male connector portion 2 and the female connector portion 3' can be connected together by hitching on the lock claws 25.

As illustrated in FIG. 10C, when the engagement surfaces 250 of the lock claws 25*a* and 25*b* engage with the first level-difference surfaces 45*a*, the abutment walls 35 of the engagement member 9 are not opposed to the second level-difference surfaces 38*b* of the lock member 90*b* in the central axis line direction A. That is, in the state of FIG. 10C, it is possible to move the lock member 90*b* from the second position (unlock position) to the first position (lock position) without interference of the abutment walls 35 and the second level-difference surfaces 38*b*. Specifically, moving the lock member 90*b* toward the distal end portion 26 of the first holder cylinder portion 21 until the first level-difference surfaces 38*a* of the lock member 90*b* abut with the abutment walls 35 makes it possible to achieve the lock position where portions of the inner peripheral surface of the lock member 90*b* connecting the first level-difference surfaces 38*a* and the second level-difference surfaces 38*b* abut with the deformation portions 31*a* and 31*b* outside the lock claws 25*a* and 25*b* in the radial direction B to inhibit the movement of the lock claws 25*a* and 25*b* outward in the radial direction B.

In this way, moving the lock member 90*b* to the lock position makes it possible to inhibit the elastic deformation and outward expansion in the radial direction B of the deformation portions 31*a* and 31*b* of the engagement member 9. Therefore, the lock claws 25 are more unlikely to come off the level-difference portions 44, and the accidental disconnection of the male connector portion 2 and the female connector portion 3' can be further suppressed.

Figure 11:
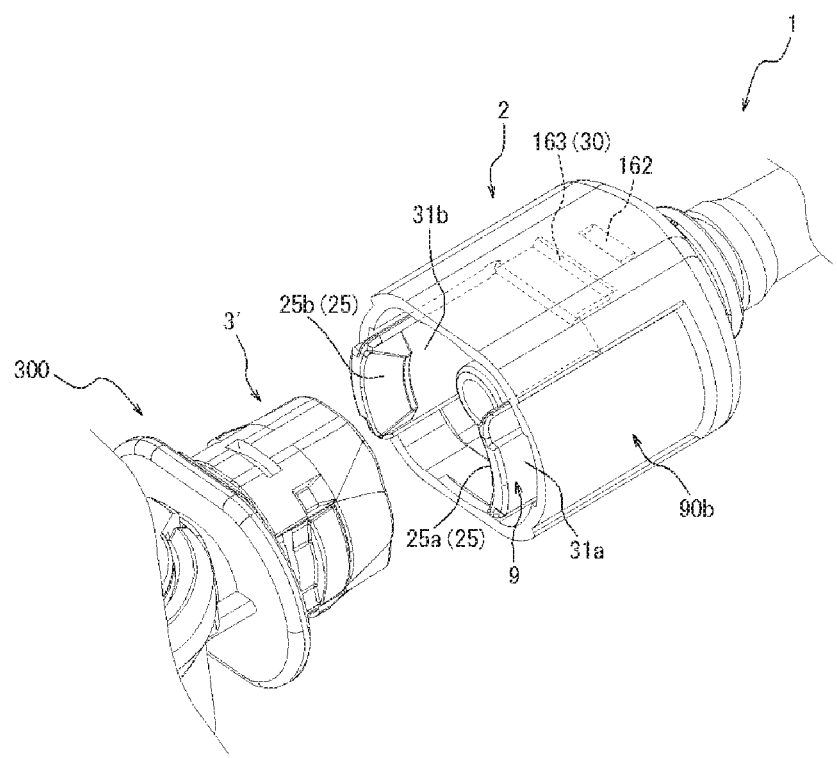
FIG. 11 is a perspective view of a male connector portion and the female connector portion illustrated in FIG. 10 before connection.

FIG. 11 is a perspective view of the male connector portion 2 and the female connector portion 3' before connection. As illustrated in FIGS. 6, 7, and 11, the inner wall of the lock member 90*b* has projection portions 162 that protrude inward. When the lock member 90*b* is moved from the second position (unlock position) to the first position (lock position), the projection portions 162 slide and pass over outer edge portions 163 of the bottom plate portion 30 of the engagement member 9.

Accordingly, even though an attempt is made to move the lock member 90b again from the first position to the second position, the projection portions 162 abuts with the upper surfaces of the outer edge flange portions 163 to inhibit the movement of the lock member 90b to the second position. In other words, the male connector portion 2 includes an inhibition mechanism that, after the connection to the female connector portion 3' of the medical device 300, inhibits the disconnection from the female connector portion 3'. In the example illustrated in FIGS. 10 and 11, the inhibition mechanism is formed from the outer edge flange portion 163 of the bottom plate portion 30 of the engagement member 9 and the projection portions 162 of the lock member 90b. Providing this inhibition mechanism makes it possible to suppress the unintentional movement of the lock member 90b from the first position to the second position. In the inhibition mechanism of the embodiment, the disconnection after connection is assumed, and the two components can be separated by external force of a predetermined value or less (for example, 15 N or less). Alternatively, without a mechanism in which the disconnection after connection is enabled, the connected components may not be separated by external force of another predetermined value or less (for example, 30 N or less) that is larger than the foregoing predetermined value.

Next, an operation of separating the male connector portion 2 and the female connector portion 3' in the connected state will be described. To disconnect the male connector portion 2 and the female connector portion 3' and remove the female connector portion 3' from the male connector portion 2, first, the lock member 90b in the first position (lock position) is moved with respect to the first holder cylinder portion 21 and the engagement member 9 in the central axis line direction A and brought into the second position (unlock position) (see the position of the lock member 90b illustrated in FIGS. 10A to 10C). Next, when one of the male connector portion 2 and the female connector portion 3' is rotated in the circumferential direction C (equal to the circumferential direction E) with respect to the other, the lock claws 25a and 25b slide on the connection slopes 65b or 65c of the bottom portions 65, and the deformation portions 31a and 31b elastically deform. As a result, the lock claws 25a and 25b move outward in the radial direction B, pass over the second level-difference surfaces 45b or the third level-difference surfaces 45c, and come out of the level-difference portions 44 and move onto the outer surfaces of the side wall portions 49. This cancels the locked state of the female connector portion 3' by the lock claws 25a and 25b.

However, as described above, since the protrusion portions 66 (see FIGS. 1A and 1B and others) are provided on the outer peripheral surfaces of the side wall portions 49, one of the male connector portion 2 and the female connector portion 3' is rotated by a predetermined distance or more in the circumferential direction C (equal to the circumferential direction E) with respect to the other such that the lock claws 25a and 25b and the protrusion portions 66 do not overlap in the central axis line direction A (equal to the central axis line direction D).

In this state, the connector 1 and the medical device 300 can be separated from each other by moving the male connector portion 2 and the female connector portion 3' to be distant from each other in the central axis line direction A.

When the lock member 90b is in the lock position, even when an attempt is made to rotate the female connector portion 3' of the medical device 300 in the circumferential direction E (equal to the circumferential direction C) with respect to the male connector portion 2 of the connector 1, the lock member 90b inhibits the elastic deformation of the deformation portions 31a and 31b of the engagement member 9 with the distal end portions widened outward in the radial direction B, and thus the lock claws 25 do not come off from the level-difference portion 44.

In this way, the main body member 90a of the connector 1 in the embodiment (see FIGS. 1A and 1B and others) includes the first cylinder portion 12 as a cylinder portion insertable into the female connector portion 3' of the medical device 300 and the lock claws 25 as lock portions that, at the insertion of the first cylinder portion 12 into the female connector portion 3', pass over the guide inclined surfaces 51 and others as part of the medical device 300 and then move in a predetermined locking direction to lock the medical device 300. Further, when the lock claws 25 locks the medical device 300, the lock member 90b of the connector 1 is movable with respect to the main body member 90a to the first position as the lock position at which to inhibit the movement of the lock claws 25 locking the medical device 300 in a predetermined unlocking direction different from the predetermined locking direction. The main body member 90a further includes the abutment walls 35 as the movement inhibition portions that inhibit the movement of the lock member 90b to the lock position while the lock claws 25 pass over the guide inclined surfaces 51 and the like of the medical device 300.

That is, the main body member 90a includes the movement inhibition portion that, while the lock portions are passing over part of the medical device 300, inhibits the movement of the lock member 90b to the lock position, and after the lock portions have passed over part of the medical device 300, permits the movement of the lock member 90b to the lock position. Accordingly, it is possible to inhibit the lock portions and part of the medical device 300 from being shaved off and worn due to repeated use because, while the lock portions pass over part of the medical device 300, the lock member 90b moves to the lock position to increase sliding resistance between the lock portions and part of the medical device 300.

Additionally, in the connector 1 of the embodiment, the insertion direction of the first cylinder portion 12 as the cylinder portion into the female connector portion 3' (one side of the central axis line direction A and the rightward direction in FIG. 10) is identical to the movement direction of the lock member 90b from the second position (unlock position) to the first position (lock position). Further, the movement inhibition portions of the embodiment are the abutment walls 35 that, at the insertion of the first cylinder portion 12 into the female connector portion 3', are opposed to the second level-difference surfaces 38b as the abutment portions of the lock member 90b in the insertion direction while the lock claws 25 as the lock portions pass over the guide inclined surfaces 51 and the like as part of the medical device 300, and then abut with the second level-difference surfaces 38b to inhibit the movement of the lock member 90b from the unlock position to the lock position. When the lock claws 25 have passed over the guide inclined surfaces 51 and the like and moved in the predetermined locking direction, the abutment walls 35 are no longer opposed to the second level-difference surfaces 38b of the lock member 90b in the insertion direction to permit the movement of the lock member 90b to the lock position.

In this way, in cooperation with the insertion of the first cylinder portion 12 of the male connector portion 2 into the female connector portion 3', the lock claws 25 as the lock portions are moved in the insertion direction, and in cooperation with the movement of the lock claws 25, the opposed state of the abutment walls 35 and the second level-difference surfaces 38b as the abutment portions to abut with the abutment walls 35 is changed. Accordingly, at the connection of the male connector portion 2 and the female connector portion 3', performing only a one-way action of bringing the male connector portion 2 and the female connector portion 3' close to each other in the central axis line direction A with the central axis lines O1 and O2 approximately aligned achieves both the connection of the male connector portion 2 and the female connector portion 3' and the movement of the lock member 90b to the lock position after the connection. Further, the lock member 90b can be moved from the unlock position to the lock position at an appropriate timing during the one-way connecting action, that is, only when the lock claws 25 have passed over part of the medical device 300. That is, the lock member 90b can be moved to the lock position at an appropriate timing by the easy connecting action.

In particular, the lock claws 25 as the lock portions of the embodiment are positioned outside the first cylinder portion 12 in the radial direction of the first cylinder portion 12. After passing over the guide inclined surfaces 51 and the like as part of the medical device 300, the lock claws 25 move inward in the radial direction B as a predetermined locking direction. According to this configuration, it is possible to implement the connection by the one-way action described above and the switching between the inhibition and permission of movement of the lock member 90b to the lock position during the connecting action.

Further, the main body member 90a of the connector 1 of the embodiment includes the engagement member 9 fixed in position with respect to the first cylinder portion 12, which has the deformation portions 31a and 31b that extend along the insertion direction outside the first cylinder portion 12 in the radial direction B and are capable of elastic deformation in the radial direction B. The lock member 90b is positioned outside the engagement member 9 in the radial direction B, and the lock claws 25 as the lock portions protrude inward in the radial direction B from the deformation portions 31a and 31b. The abutment walls 35 as the movement inhibition portions are formed on the outer walls of the deformation portions 31a and 31b outward in the radial direction B. Configuring the connector 1 of the embodiment as described above makes it possible to achieve the connection by the one-way action and the switching between the inhibition and permission of the movement of the lock member 90b to the lock position during the connecting action by using a series of elastic deformations of the deformation portions 31a and 31b that are widened outward in the radial direction B at the time of connection and then are returned inward in the radial direction B by resilience. This allows a simpler and highly operable configuration with a relatively small sliding resistance at the movement of the lock member 90b to the lock position.

In addition, the female connector portion 3' of the medical device 300 connectable to the connector 1 is formed at least partially by the first cap 18 as a cap defining the first insertion opening 80 as an insertion hole into which the first cylinder portion 12 of the connector 1 is inserted and the holder 17 that defines the flow path communicating with the first insertion opening 80 and supports the first cap 18. The first cap 18 includes the guide inclined surfaces 51 as the first slide portions that the lock claws 25 as the lock portions slide on and pass over at the insertion of the first cylinder portion 12 into the first insertion opening 80. The holder 17 includes the connection slopes 65b and 65c as the second slide portions that the lock claws 25 slide on and pass over when the lock claws 25 having passed over the guide inclined surfaces 51 and moved in the predetermined locking direction move in the predetermined unlocking direction. Configuring the female connector portion 3' of the medical device 300 in this manner makes it possible to provide separately the portions on which the lock claws 25 slide at the connection to the male connector portion 2 and the portions on which the lock claws 25 slide at the removal from the male connector portion 2. This inhibits the female connector portion 3' from being locally shaved off.

Figure 13:
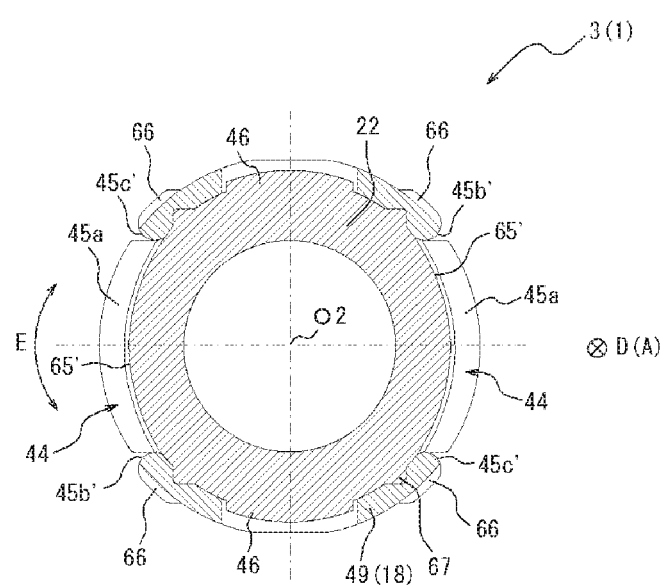
FIG. 13 is a view illustrating a modification example of level-difference portions in a second holder cylinder portion and a side wall portion of a first cap illustrated in FIG. 9.

The bottom portions 65 of the level-difference portions 44 of the connector 1 in the embodiment have the connection slopes 65b and 65c as the second slide portions on the both side in the circumferential direction E. Alternatively, the connector 1 of the embodiment may have bottom portions 65' without the connection slopes 65b and 65c as illustrated in FIG. 13, for example. In such a case, second level-difference surfaces 45b' and third level-difference surfaces 45c' of the side wall portions 49 of the first cap 18 constitute the second slide portions. The second level-difference surfaces 45b' and the third level-difference surfaces 45c' as the second slide portions are preferably surfaces with a curve at least at edges continued to the outer peripheral surfaces of the side wall portions 49 (see FIG. 13) or inclined surfaces in which the radial distance from the central axis line O2 gradually increases outward in the circumferential direction E of the bottom portions 65'.

Configuring the second level-difference surfaces 45b' and the third level-difference surfaces 45c' in this manner makes it easier to move the lock claws 25 onto the outer surfaces of the side wall portions 49 while sliding on the second level-difference surfaces 45b' and the third level-difference surfaces 45c' as compared to the configuration in which the second and third level-difference surfaces are approximately orthogonal to the bottom portions 65'. However, when the lock claws 25 slide on the second level-difference surfaces 45b' and the third level-difference surfaces 45c', the first cap 18 is likely to rotate in the circumferential direction E with respect to the second holder cylinder portion 22 by the force of the lock claws 25 pressing the second level-difference surfaces 45b' or the third level-difference surfaces 45c' in the circumferential direction E. Accordingly, as illustrated in FIG. 13, the outer surface of the second holder cylinder portion 22 particularly preferably has the convex portions 67 to fit into the concave portions on the inner surfaces of the side wall portions 49 in addition to the projection portions 46. Thus, even when the bottom portions 65 do not have the connection slopes 65b and 65c as illustrated in FIG. 13, the projection portions 46 and the convex portions 67 inhibit more reliably the rotation of the first cap 18 in the circumferential direction E with respect to the second holder cylinder portion 22. The connector 1 illustrated in FIG. 13 is similar in configuration to the connector 1 illustrated in FIGS. 1 to 9 except for the points described above.

In this manner, the second slide portions may be provided in the holder 17 as in the embodiment (see FIG. 9) or may be provided in the first cap 18 as in a modification example (see FIG. 13). However, when the first cap 18 of the female connector portion 3' in the medical device 300 is made from a material harder than that for the holder 17, the second slide portions are preferably formed by the second level-difference surfaces 45b and the third level-difference surfaces 45c of the first cap 18 as illustrated in FIG. 13 rather than by the holder 17. This further reduces wear of the second slide portions by sliding on the lock portions of the connector 1. Specifically, when the first cap 18 is formed from a polyacetal resin (POM) and the holder 17 is formed from a polypropylene resin (PP), the second slide portions are preferably formed by the second level-difference surfaces 45b and the third level-difference surfaces 45c of the first cap 18 as illustrated in FIG. 13 because the polyacetal resin is harder than the polypropylene resin.

In the embodiment, the predetermined locking direction is the inward side of the radial direction B of the first cylinder portion 12. In the embodiment, the predetermined unlocking direction is the outward side of the radial direction B of the first cylinder portion 12. The connection slopes 65b and 65c as the second slide portions in the embodiment become adjacent to the lock claws 25 as the lock portions that have passed over the guide inclined surfaces 51 as the first slide portions and moved to the inward side of the radial direction B, in the circumferential direction C of the first cylinder portion 12. In the modification example illustrated in FIG. 13 as well, the second level-difference surfaces 45b and the third level-difference surfaces 45c as the second slide portions become adjacent to the lock claws 25 as the lock portions that have passed over the guide inclined surfaces 51 as the first slide portions and moved to the inward side of the radial direction B, in the circumferential direction C of the first cylinder portion 12. Configuring the female connector portion 3' of the medical device 300 in this manner and aligning the movement direction of the male connector portion 2 of the connector 1 with respect to the main body member 90a of the lock member 90b to the central axis line direction A makes it possible to, at the removal of the female connector portion 3' from the male connector portion 2, move the lock member 90b in the central axis line direction A to move the lock member 90b from the lock position to the unlock position, and then rotating one of the male connector portion 2 and the female connector portion 3' with respect to the other to unlock the female connector portion 3' from the lock claws 25a and 25b. That is, to remove the female connector portion 3' from the male connector portion 2, different two-way actions need to be performed. Therefore, according to the connector 1 and the medical device 300 of the embodiment, the connecting operation is easy and the unintentional disconnection after the connection is unlikely to occur with high safety.

The connector 1 in the embodiment is called T-shaped connector including the male connector portion 2, the first female connector portion 3, and the second female connector portion 4. However, the connector 1 is not limited to the T-shaped connector but may be any other connector with the male connector portion 2. For example, the connector 1 may be formed from a three-way stopcock that includes a cock and a holder storing the cock and having three ports, one of the ports being similar in configuration to the male connector portion 2. Further, the connector 1 may be a connector in which the first female connector portion 3 and the second female connector portion 4 are different in shape or either the first female connector portion 3 or the second female connector portion 4 is nonexistent without a plurality of flow paths.

The medical device 300 may be equal in shape to the connector 1 or may be different in shape from the connector 1, for example, as far as the medical device 300 includes the female connector portion 3' connectable to the male connector portion 2 of the connector 1. Alternatively, any other medical device may include the female connector portion 3'.

[Infusion Set 200]

Finally, an infusion set 200 including the connector 1 as an embodiment of the present invention will be described.

Figure 12:
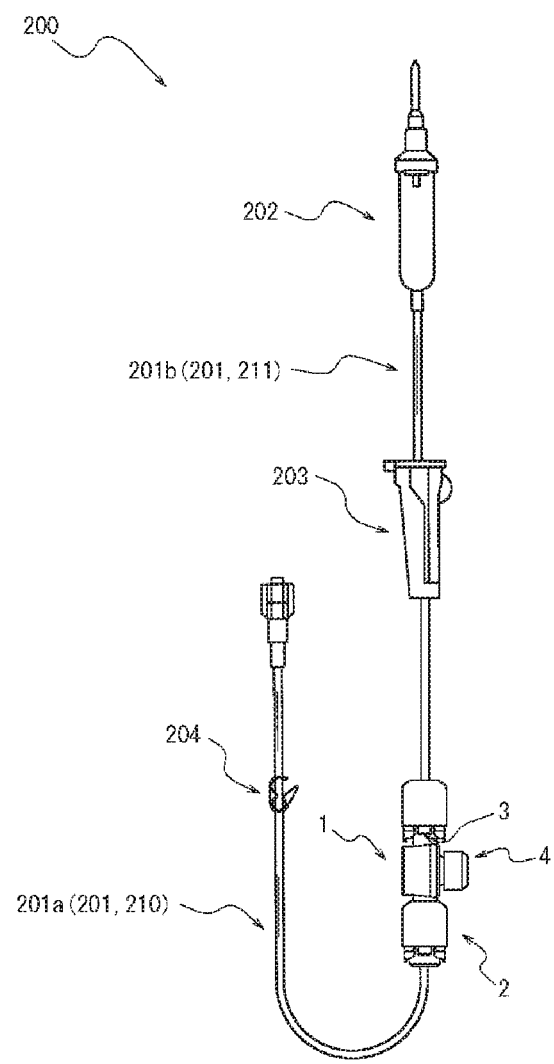
FIG. 12 is a view illustrating an infusion set according to one embodiment of the present invention.

FIG. 12 is a view of an infusion set 200 including the connector 1. The infusion set 200 illustrated in FIG. 12 includes a T-shaped connector as the connector 1. Alternatively, the infusion set may include a three-way stopcock instead of the T-shaped connector. For the sake of convenience, the infusion set 200 including the T-shaped connector as the connector 1 will be described here.

The infusion set 200 constitutes an infusion line connecting an infusion holding instrument such as an infusion bag not illustrated in FIG. 12 to an indwelling needle not illustrated in FIG. 12. Specifically, the infusion set 200 includes a plurality of medical tubes 201, a drip tube 202 through which the flow rate of an infusion fluid supplied from the infusion holding instrument is visible, an adjustment clamp 203 that is capable of changing the flow rate of the infusion fluid in the medical tubes 201 to a plurality of states, a block clamp 204 that blocks the medical tubes 201, and the connector 1 connecting the plurality of medical tubes 201.

In other words, the infusion set 200 of the embodiment includes the connector 1, a first medical device 210 that has at the upstream end portion a female connector portion equal in shape to the first female connector portion 3 of the connector 1, as a female connector portion connected to the male connector portion 2 of the connector 1, and a second medical device 211 that has at the downstream end portion, a male connector portion equal in shape to the male connector portion 2 of the connector 1, as a male connector portion connected to the first female connector portion 3 of the connector 1.

The plurality of medical tubes 201 in the embodiment includes a first medical tube 201a and a second medical tube 201b. The first medical device 210 in the embodiment is formed from the first medical tube 201a that has an ISO594-prescribed lock-type male connector portion at the downstream end portion and a female connector portion equal in shape to the first female connector portion 3 of the connector 1 at the upstream end portion.

In addition, the second medical device 211 in the embodiment is formed from the second medical tube 201b that has a male connector portion equal in shape to the male connector portion 2 of the connector 1 at the downstream end portion and a bottle needle to be connected to the infusion holding instrument at the upstream end portion.

Then, the upstream end portion of the infusion line in the infusion set 200 illustrated in FIG. 12 is connected to the infusion holding instrument and the downstream end portion thereof is connected to the indwelling needle to inject the infusion fluid to a patient. In addition, when there is the need to administer another infusion fluid according to the patient's condition or the like, a branch line can be connected to the second female connector portion 4 of the connector 1.

In the infusion set 200 of the embodiment, the medical tubes 201a and 201b are used as the first medical device 210 including the female connector portion to be connected to the male connector portion 2 of the connector 1 and the second medical device 211 including the male connector portion to be connected to the first female connector portion 3 of the connector 1. However, the medical devices are not limited to medical tubes but may be any medical devices other than medical tubes such as a connector equal in shape to the connector 1 and a connector different in shape from the connector 1. In addition, the first medical device and the second medical device may be formed from a plurality of devices in combination or may be formed from a single device.

The connector, the infusion set, and the medical device connectable to the connector according to the present invention are not limited to the configurations specified in the foregoing embodiments, but rather can be modified in various manner without deviating from the gist of the invention recited in the claims. For example, the movement inhibition portions and the abutment portions of the connector 1 in the embodiment are formed from the abutment walls 35 and the level-difference surfaces 38b. However, the movement inhibition portions and the abutment portions are not limited to the abutment walls 35 and the level-difference surfaces 38b of the embodiment as far as they are configured to switch between the inhibition and permission of the movement of the lock member 90b to the lock position in accordance with the positions of the lock portions. However, employing the configuration in which part of the main body member 90a and part of the lock member 90b are brought into direct abutment with each other as with the abutment walls 35 and the level-difference surfaces 38b of the embodiment makes it possible to achieve the switching between the inhibition and permission of the movement of the lock member 90b to the lock position in an easy and more reliably manner.

The lock position of the lock member 90b in the connector 1 is not limited to the position where the movement of the lock claws 25 in the unlocking direction is not permitted at all (the movable amount of the lock claws 25 is zero), for example, as far as the amount of movement of the lock claws 25 in the unlocking direction is limited to a predetermined amount or less so that the medical device is not unlocked from the lock claws 25. The lock portions of the connector 1 are the lock claws 25 that pass over the guide inclined surfaces 51 as the first slide portions. However, the shapes and positions of the lock portions and the first slide portions are not limited to the shapes and positions of the lock claws 25 and the guide inclined surfaces 51 as far as, after passing over part of the medical device, the lock portions move in the predetermined locking direction to lock the medical device.

The present disclosure relates to a connector, an infusion set, and a medical device connectable to the connector.

REFERENCE NUMERAL LIST

1 Connector
2 Male connector portion
3 First female connector portion
3' Female connector portion
4 Second female connector portion
5 Flow path
6 Housing
7 First elastic valve body
8 Second elastic valve body
9 Engagement member
11 Housing trunk portion
11a Trunk hollow portion
12 First cylinder portion (cylinder portion)
12a First hollow portion
13 Second cylinder portion
13a Second hollow portion
14 Third cylinder portion
14a Third hollow portion
15 Slit in first elastic valve body
16 Slit in second elastic valve body
17 Holder
18 First cap (cap)
19 Second cap
20 Holder main body
21 First holder cylinder portion
22 Second holder cylinder portion
22a Annular flange portion
23 Upper cap
24 Lower cap
25, 25a, 25b Lock claw (lock portion)
26 Distal end portion of first holder cylinder portion
27 Long groove
28 Division portion
29 Protrusion portion (connection inhibition portion)
30 Bottom plate portion of engagement member
31a, 31b Deformation portion of engagement member
32 Concave portion
34 Rib
35 Abutment wall (movement inhibition portion)
36 Bottom plate portion of lock member
37 Cover cylinder portion
38a First level-difference surface of lock member
38b Second level-difference surface of lock member (abutment portion)
39 Concave portion
40 Curved portion
41 Flat plate portion
42 Upper annular groove in first elastic valve body
43 Lower annular groove in first elastic valve body
44 Level-difference portion
45a First level-difference surface
45b, 45b' Second level-difference surface (second slide portion)
45c, 45c' Third level-difference surface (second slide portion)
46 Projection portion of second holder cylinder portion
47 Lock projection of second holder cylinder portion
48 Top plate portion of first cap
49 Side wall portion of first cap
50 Lock projection of first cap
51 Guide inclined surface (first slide portion)
55 Top plate portion of upper cap
55a Inner peripheral surface of top plate portion
56 Cylinder portion of upper cap
57 Flange portion of upper cap
59 Male screw portion
60 Cylinder portion of lower cap
61 Flange portion of lower cap
65, 65' Bottom portion
65b, 65c Connection slope
66 Protrusion portion
67 Convex portion
68 Reception portion
80 First insertion opening (insertion opening)
81 Second insertion opening
90a Main body member
90b Lock member
162 Protrusion portion of lock member
163 Outer edge flange portion of engagement member
200 Infusion set
201 Medical tube
201a First medical tube
201b Second medical tube
202 Drip tube
203 Adjustment clamp
204 Block clamp
210 First medical device
211 Second medical device

250 Engagement surface of lock claw
300 Medical device
400 Connector connection body
A Central axis line direction of first holder cylinder portion
B Radial direction of first holder cylinder portion
C Circumferential direction of first holder cylinder portion
D Central axis line direction of second holder cylinder portion (central axis line direction of inner wall defining first insertion opening)
E Circumferential direction of second holder cylinder portion
F Radial direction of second holder cylinder portion
G Central axis line direction of cylinder portion of upper cap (central axis line direction of inner wall defining second insertion opening)
$O1$ Central axis line of first holder cylinder portion
$O2$ Central axis line of inner wall defining first insertion opening
$O3$ Central axis line of inner wall defining second insertion opening
$T1$ Thickness of bottom plate portion
$W1$ Width of long groove
$W2$ Width of concave portion oriented in circumferential direction
$W3$ Width of division portion oriented in circumferential direction

What is claimed is:

1. A connector that is connectable to a medical device that comprises a female connector portion, the connector comprising:
    a main body member comprising:
        a cylinder portion that is insertable into the female connector portion of the medical device, and
        an engagement member that is fixed in position with respect to the cylinder portion, the engagement member comprising:
            a deformation portion that extends in an insertion direction, the insertion direction being a direction in which the cylinder portion is insertable into the female connector portion, the deformation portion being located at a position outside the cylinder portion in a radial direction of the cylinder portion and being elastically deformable in the radial direction, and
            a lock portion located at a distal end of the deformation portion, the lock portion being configured to, upon insertion of the cylinder portion into the female connector portion, pass over part of the medical device and then move in a radially inward locking direction to lock the medical device to the connector; and
        a lock member that is movable with respect to the main body member, wherein the lock member is configured such that, when the main body member is in a state in which the lock portion locks the medical device to the connector, the lock member is moveable to a lock position at which the lock member limits movement of the lock portion in a radially outward unlocking direction;
    wherein the lock member is positioned outside the engagement member in the radial direction and comprises, at an inner surface of the lock member, a level-difference surface that is perpendicular to a longitudinal axis of the lock member and that faces in a distal direction when the lock member is in the lock position;
    wherein the engagement member comprises, at an outer wall of the deformation portion, an abutment wall having an abutment wall surface that is perpendicular to a longitudinal axis of the engagement member and that faces in a proximal direction when the lock member is in the lock position; and
    wherein the abutment wall is configured to inhibit movement of the lock member to the lock position while the lock portion passes over said part of the medical device by abutting the level-difference surface when the deformation portion is deformed in the radially outward unlocking direction.

2. The connector according to claim 1, wherein:
    the abutment wall is configured to allow movement of the lock member to the lock position after the lock portion passes over said part of the medical device and moves in the radially inward locking direction by not abutting the level-difference surface when the deformation portion is not deformed in the radially outward unlocking direction.

3. The connector according to claim 1, wherein:
    the lock portion comprises a lock claw that protrudes inward from the deformation portion in the radial direction.

4. The connector according to claim 3, wherein:
    the lock member comprises a reception portion configured to receive at least part of the deformation portion elastically deformed in the radial direction; and
    the level-difference surface is located in the reception portion.

5. An infusion set comprising the connector according to claim 1.

6. A method of using an assembly comprising a medical device and a connector, the method comprising:
    providing a medical device that comprises a female connector portion;
    providing a connector that comprises:
        a main body member comprising:
            a cylinder portion that is insertable into the female connector portion of the medical device, and
            an engagement member that is fixed in position with respect to the cylinder portion, the engagement member comprising:
                a deformation portion that extends in an insertion direction, the insertion direction being a direction in which the cylinder portion is insertable into the female connector portion, the deformation portion being located at a position outside the cylinder portion in a radial direction of the cylinder portion and being elastically deformable in the radial direction, and
                a lock portion located at a distal end of the deformation portion, the lock portion being configured to, upon insertion of the cylinder portion into the female connector portion, pass over part of the medical device and then move in a radially inward locking direction to lock the medical device to the connector, and
            a lock member that is movable with respect to the main body member, wherein the lock member is configured such that, when the main body member is in a state in which the lock portion locks the medical device to the connector, the lock member is moveable to a lock position at which the lock member limits movement of the lock portion in a radially outward unlocking direction;

wherein the lock member is positioned outside the engagement member in the radial direction and comprises, at an inner surface of the lock member, a level-difference surface that is perpendicular to a longitudinal axis of the lock member and that faces in a distal direction when the lock member is in the lock position, and wherein the engagement member comprises, at an outer wall of the deformation portion, an abutment wall having an abutment wall surface that is perpendicular to a longitudinal axis of the engagement member and that faces in a proximal direction when the lock member is in the lock position;

inserting the cylinder portion into the female connector portion;

causing the lock portion to pass over said part of the medical device; and inhibiting movement of the lock member to the lock position while the lock portion passes over said part of the medical device by the abutment wall abutting the level-difference surface when the deformation portion is deformed in the radially outward unlocking direction.

\* \* \* \* \*

UNITED STATES PATENT AND TRADEMARK OFFICE
CERTIFICATE OF CORRECTION

PATENT NO. : 10,881,848 B2
APPLICATION NO. : 15/938781
DATED : January 5, 2021
INVENTOR(S) : Ueda It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 177 days.

Signed and Sealed this
Thirty-first Day of January, 2023

Katherine Kelly Vidal
*Director of the United States Patent and Trademark Office*